US011672561B2

(12) United States Patent
Look et al.

(10) Patent No.: US 11,672,561 B2
(45) Date of Patent: Jun. 13, 2023

(54) SYSTEMS AND METHODS FOR MANIPULATING MEDICAL DEVICES

(71) Applicant: Walk Vascular, LLC, Irvine, CA (US)

(72) Inventors: David M. Look, Newport Beach, CA (US); Bradley S. Culbert, Mission Viejo, CA (US)

(73) Assignee: WALK VASCULAR, LLC, Irvine, CA (US)

( * ) Notice: Subject to any disclaimer, the term of this patent is extended or adjusted under 35 U.S.C. 154(b) by 579 days.

(21) Appl. No.: 16/721,151

(22) Filed: Dec. 19, 2019

(65) Prior Publication Data

US 2020/0121356 A1 Apr. 23, 2020

Related U.S. Application Data

(63) Continuation of application No. 15/256,488, filed on Sep. 2, 2016, now Pat. No. 10,561,440.

(Continued)

(51) Int. Cl.

*A61B 17/3207* (2006.01)
*A61B 17/3203* (2006.01)

(Continued)

(52) U.S. Cl.

CPC ...... *A61B 17/320758* (2013.01); *A61B 17/22* (2013.01); *A61B 17/32037* (2013.01);

(Continued)

(58) Field of Classification Search

CPC ........ A61B 17/3207; A61B 17/320725; A61B 17/32075; A61B 17/320758;

(Continued)

(56) References Cited

U.S. PATENT DOCUMENTS 1,114,268 A 10/1914 Kells
1,144,268 A 6/1915 Vickery (Continued)

FOREIGN PATENT DOCUMENTS

CN 1120805 A 4/1996
CN 201079629 Y 7/2008

(Continued)

OTHER PUBLICATIONS

PCT International Search Report and Written Opinion for PCT/US2016/050302. Applicant Vesatek, LLC. Forms PCT/ISA/220, 210, and 237 dated Nov. 29, 2016 (10 pages).

(Continued)

*Primary Examiner* — Dianne Dornbusch
(74) *Attorney, Agent, or Firm* — Workman Nydegger; Randy Shen

(57) ABSTRACT

A method for treating a patient having thrombus includes providing a manipulation device including a housing configured to be supported by the hand of a user and having a distal and proximal end, a drive system disposed within the housing, and configured to rotate a rotation member, an engagement member coupled to the rotation member and configured to be removably coupled to an elongate medical device, an activation member carried by the housing such that it can be operated by at least a portion of the hand of the user when the housing is supported by the hand of the user, the drive system configured to apply motive force to the engagement member, securing an elongate member to the engagement member, introducing at least the distal end of the elongate member into a blood vessel adjacent a thrombus, operating the activation member to cause at least some rotation of the rotation member, which in turn causes at least some rotation of the distal end of the elongate member at or (Continued)

near the thrombus, and aspirating at least some of the thrombus with an aspiration catheter.

20 Claims, 23 Drawing Sheets

Related U.S. Application Data

(60) Provisional application No. 62/286,429, filed on Jan. 24, 2016, provisional application No. 62/214,192, filed on Sep. 3, 2015.

(51) Int. Cl.
*A61B 17/22* (2006.01)
*A61B 17/00* (2006.01)

(52) U.S. Cl.
CPC ............... *A61B 2017/00017* (2013.01); *A61B 2017/00367* (2013.01); *A61B 2017/00398* (2013.01); *A61B 2017/00469* (2013.01); *A61B 2017/00685* (2013.01); *A61B 2017/00734* (2013.01); *A61B 2017/22038* (2013.01); *A61B 2017/22042* (2013.01); *A61B 2017/22044* (2013.01); *A61B 2017/22049* (2013.01); *A61B 2017/22079* (2013.01); *A61B 2017/22094* (2013.01); *A61B 2217/005* (2013.01); *A61B 2217/007* (2013.01)

(58) Field of Classification Search
CPC .......... A61B 17/3203; A61B 17/32032; A61B 17/32035; A61B 17/32037; A61B 17/22; A61B 2217/002; A61B 2217/005; A61B 2217/007
See application file for complete search history.

(56) References Cited

U.S. PATENT DOCUMENTS 1,148,093 A 7/1915 Kells
2,804,075 A 8/1957 Borden
3,429,313 A 2/1969 Romanelli
3,494,363 A 2/1970 Richard
3,589,363 A 6/1971 Banko et al.
3,620,650 A 11/1971 Shaw
3,631,847 A 1/1972 Hobbs, II
3,693,613 A 9/1972 Kelman
3,707,967 A 1/1973 Kitrilakis et al.
3,748,435 A 7/1973 Reynolds
3,807,401 A 4/1974 Bennett et al.
3,818,913 A 6/1974 Wallach
3,847,140 A 11/1974 Ayelia
3,916,892 A 11/1975 Latham, Jr.
3,918,453 A 11/1975 Leonard
3,930,505 A 1/1976 Wallach
3,955,573 A 5/1976 Hansen et al.
4,030,503 A 6/1977 Clark, III
4,274,411 A 6/1981 Dotson, Jr.
4,299,221 A 11/1981 Phillips et al.
4,465,470 A 8/1984 Keiman
4,573,476 A 3/1986 Ruiz
4,574,812 A 3/1986 Arkans
4,638,539 A 1/1987 Palmer
4,690,672 A 9/1987 Veltrup
4,700,705 A 10/1987 Kensey et al.
4,702,733 A 10/1987 Wright et al.
4,715,853 A 12/1987 Prindle
4,728,319 A 3/1988 Masch
4,740,203 A 4/1988 Hoskins et al.
4,747,821 A 5/1988 Kensey et al.
4,747,834 A 5/1988 Prindle
4,770,654 A 9/1988 Rogers et al.
4,784,157 A 11/1988 Halls et al.
4,790,813 A 12/1988 Kensey
4,832,685 A 5/1989 Haines
4,842,579 A 6/1989 Shiber
4,854,325 A 8/1989 Stevens
4,857,046 A 8/1989 Stevens et al.
4,883,458 A 11/1989 Shiber
4,883,467 A 11/1989 Franetzki et al.
4,886,490 A 12/1989 Shiber
4,886,507 A 12/1989 Patton et al.
4,894,051 A 1/1990 Shiber
4,898,574 A 2/1990 Uchiyama et al.
4,957,482 A 9/1990 Shiber
4,979,939 A 12/1990 Shiber
4,998,919 A 3/1991 Schnepp-Pesch
5,002,553 A 3/1991 Shiber
5,007,896 A 4/1991 Shiber
5,011,468 A 4/1991 Lundquist et al.
5,011,488 A 4/1991 Ginsburg
5,024,651 A 6/1991 Shiber
5,055,109 A 10/1991 Gould et al.
5,057,098 A 10/1991 Zelman
5,064,428 A 11/1991 Cope et al.
5,073,164 A 12/1991 Hollister et al.
5,073,168 A 12/1991 Danforth
5,074,841 A 12/1991 Ademovic et al.
5,078,722 A 1/1992 Stevens
5,091,656 A 2/1992 Gahn
5,125,893 A 6/1992 Dryden
5,129,887 A 7/1992 Euteneuer et al.
5,135,482 A 8/1992 Neracher
5,135,531 A 8/1992 Shiber
5,158,564 A 10/1992 Schnepp-Pesch et al.
5,163,433 A 11/1992 Kagawa et al.
5,195,954 A 3/1993 Schnepp-Pesch et al.
5,197,795 A 3/1993 Mudrovich
5,197,951 A 3/1993 Mahurkar
5,234,407 A 8/1993 Teirstein et al.
5,242,404 A 9/1993 Conley et al.
5,243,997 A 9/1993 Uflacker et al.
5,248,297 A 9/1993 Takase
5,254,085 A 10/1993 Cleveland
5,261,877 A 11/1993 Fine et al.
5,284,486 A 2/1994 Kotula et al.
5,290,247 A 3/1994 Crittenden
5,306,244 A 4/1994 Shiber
5,312,427 A 5/1994 Shturman
5,318,518 A 6/1994 Plechinger et al.
5,318,529 A 6/1994 Kontos
5,320,604 A 6/1994 Walker et al.
5,322,504 A 6/1994 Doherty et al.
5,324,263 A 6/1994 Kraus et al.
5,325,868 A 7/1994 Kimmelstiel
5,327,906 A 7/1994 Fideler
5,334,211 A 8/1994 Shiber
5,342,293 A 8/1994 Zanger
5,342,306 A 8/1994 Don Michael
5,356,375 A 10/1994 Higley
5,368,555 A 11/1994 Sussman et al.
5,370,609 A 12/1994 Drasler et al.
5,385,562 A 1/1995 Adams et al.
5,389,072 A 2/1995 Imran
5,392,778 A 2/1995 Horzewski
5,395,315 A 3/1995 Griep
5,403,274 A 4/1995 Cannon
5,403,276 A 4/1995 Schechter et al.
5,413,561 A 5/1995 Fischell et al.
5,419,772 A 5/1995 Teitz et al.
5,421,826 A 6/1995 Crocker et al.
5,429,601 A 7/1995 Conley et al.
5,443,078 A 8/1995 Uflacker
5,443,443 A 8/1995 Shiber
5,476,450 A 12/1995 Ruggio
5,478,331 A 12/1995 Heflin et al.
5,486,183 A 1/1996 Middleman et al.
5,490,837 A 2/1996 Blaeser et al.
5,496,267 A 3/1996 Drasler et al.
5,507,738 A 4/1996 Ciervo
5,524,180 A 6/1996 Wang et al.
5,524,635 A 6/1996 Uflacker et al.

(56) References Cited

U.S. PATENT DOCUMENTS 5,527,274 A 6/1996 Zakko
5,536,242 A 7/1996 Willard et al.
5,538,002 A 7/1996 Boussignac et al.
5,562,692 A 10/1996 Bair
5,569,275 A 10/1996 Kotula et al.
5,577,674 A 11/1996 Altonji et al.
5,605,545 A 2/1997 Nowosielski et al.
5,606,968 A 3/1997 Mang
5,624,394 A 4/1997 Bamitz et al.
5,626,563 A 5/1997 Dodge et al.
5,634,475 A 6/1997 Wolvek
5,647,847 A 7/1997 Lafontaine et al.
5,653,696 A 8/1997 Shiber
5,660,180 A 8/1997 Malinowski et al.
5,669,876 A 9/1997 Schechter et al.
5,695,507 A 12/1997 Auth et al.
5,709,661 A 1/1998 Van Egmond et al.
5,713,849 A 2/1998 Bosma et al.
5,713,851 A 2/1998 Boudewijn et al.
5,713,878 A 2/1998 Moutafis et al.
5,730,717 A 3/1998 Gelbfish
5,735,535 A 4/1998 McCombs et al.
5,766,191 A 6/1998 Trerotola
5,772,674 A 6/1998 Nakhjavan
5,785,685 A 7/1998 Kugler et al.
5,795,322 A 8/1998 Boudewijn
5,795,332 A 8/1998 Lucas et al.
5,810,770 A 9/1998 Chin et al.
5,827,229 A 10/1998 Auth et al.
5,827,243 A 10/1998 Palestrant
5,833,644 A 11/1998 Zadno-Azizi et al.
5,843,022 A 12/1998 Willard et al.
5,843,051 A 12/1998 Adams et al.
5,853,384 A 12/1998 Bair
5,855,567 A 1/1999 Ressemann
5,868,702 A 2/1999 Stevens et al.
5,871,462 A 2/1999 Yoder et al.
5,876,414 A 3/1999 Straub
5,885,238 A 3/1999 Stevens et al.
5,885,244 A 3/1999 Leone et al.
5,893,857 A 4/1999 Shturman et al.
5,895,398 A 4/1999 Wensel et al.
5,895,399 A 4/1999 Barbut et al.
5,908,395 A 6/1999 Stalker et al.
5,910,252 A 6/1999 Truitt et al.
5,911,722 A 6/1999 Adler et al.
5,916,192 A 6/1999 Nita et al.
5,921,958 A 7/1999 Ressemann et al.
5,938,645 A 8/1999 Gordon
5,941,871 A 8/1999 Adams et al.
5,944,686 A 8/1999 Patterson et al.
5,957,901 A 9/1999 Mottola et al.
5,989,210 A 11/1999 Morris et al.
5,989,271 A 11/1999 Bonnette et al.
6,001,112 A 12/1999 Taylor
6,007,513 A 12/1999 Anis et al.
6,019,728 A 2/2000 Iwata et al.
6,022,336 A 2/2000 Zadno-Azizi et al.
6,027,460 A 2/2000 Shturman
6,080,170 A 6/2000 Nash et al.
6,090,118 A 7/2000 McGuckin, Jr.
6,096,001 A 8/2000 Drasler et al.
6,126,635 A 10/2000 Simpson et al.
6,129,697 A 10/2000 Drasler et al.
6,129,698 A 10/2000 Beck
6,146,355 A 11/2000 Biggs
6,146,396 A 11/2000 Kńya et al.
6,152,909 A 11/2000 Bagaoisan et al.
6,156,046 A 12/2000 Passafaro et al.
6,159,230 A 12/2000 Samuels
6,165,188 A 12/2000 Saadat et al.
6,176,844 B1 1/2001 Lee
6,179,809 B1 1/2001 Khairkhahan et al.
6,179,851 B1 1/2001 Barbut et al.
6,183,432 B1 2/2001 Milo
6,190,357 B1 2/2001 Ferrari et al.
6,196,989 B1 3/2001 Padget et al.
6,206,898 B1 3/2001 Honeycutt et al.
6,216,573 B1 4/2001 Moutafis et al.
6,224,570 B1 5/2001 Le et al.
6,238,405 B1 5/2001 Findlay, III et al.
6,258,061 B1 7/2001 Drasler et al.
6,283,719 B1 9/2001 Frantz et al.
6,293,960 B1 9/2001 Ken
6,331,171 B1 12/2001 Cohen
6,348,040 B1 2/2002 Stalker et al.
6,375,635 B1 4/2002 Moutafis et al.
6,423,032 B2 7/2002 Parodi
6,440,148 B1 8/2002 Shiber
6,454,741 B1 9/2002 Muni et al.
6,454,775 B1 9/2002 Demarais et al.
6,471,683 B2 10/2002 Drasler et al.
6,481,439 B1 11/2002 Lewis et al.
6,488,672 B1 12/2002 Dance et al.
6,508,823 B1 1/2003 Gonon
6,533,772 B1 3/2003 Sherts et al.
6,544,209 B1 4/2003 Drasler et al.
6,544,231 B1 4/2003 Palmer et al.
6,551,302 B1 4/2003 Rosinko et al.
6,554,794 B1 4/2003 Mueller et al.
6,554,799 B1 4/2003 Hatamura et al.
6,558,366 B1 5/2003 Drasler et al.
6,558,401 B1 5/2003 Azizi
6,569,147 B1 5/2003 Evans et al.
6,569,148 B2 5/2003 Bagaoisan et al.
6,572,578 B1 6/2003 Blanchard
6,579,270 B2 6/2003 Sussman et al.
6,585,705 B1 7/2003 Maginot et al.
6,599,271 B1 7/2003 Easley
6,615,835 B1 9/2003 Cise et al.
6,616,679 B1 9/2003 Khosravi et al.
6,622,367 B1 9/2003 Bolduc et al.
6,623,495 B2 9/2003 Findlay, III et al.
6,635,034 B1 10/2003 Cosmescu
6,635,070 B2 10/2003 Leeflang et al.
6,638,235 B2 10/2003 Miller et al.
6,652,546 B1 11/2003 Nash et al.
6,652,548 B2 11/2003 Evans et al.
6,663,613 B1 12/2003 Evans et al.
6,669,710 B2 12/2003 Moutafis et al.
6,676,637 B1 1/2004 Bonnette et al.
6,702,830 B1 3/2004 Demarais et al.
6,719,717 B1 4/2004 Johnson et al.
6,723,081 B1 4/2004 Hektner
6,726,675 B1 4/2004 Beyer
6,752,800 B1 6/2004 Winston et al.
6,755,803 B1 6/2004 Le et al.
6,755,812 B2 6/2004 Peterson et al.
6,790,215 B2 9/2004 Findlay, III et al.
6,805,684 B2 10/2004 Bonnette et al.
6,818,001 B2 11/2004 Wulfman et al.
6,824,545 B2 11/2004 Sepetka et al.
6,824,550 B1 11/2004 Noriega et al.
6,830,577 B2 12/2004 Nash et al.
6,875,193 B1 4/2005 Bonnette et al.
6,899,712 B2 5/2005 Moutafis et al.
6,926,726 B2 8/2005 Drasler et al.
6,929,633 B2 8/2005 Evans et al.
6,936,056 B2 8/2005 Nash et al.
6,945,977 B2 9/2005 Demarais et al.
6,958,059 B2 10/2005 Zadno-Azizi
6,984,239 B1 1/2006 Drasler et al.
6,986,778 B2 1/2006 Zadno-Azizi
6,991,625 B1 1/2006 Gately et al.
7,008,434 B2 3/2006 Kurz et al.
7,044,958 B2 5/2006 Douk et al.
7,108,704 B2 9/2006 Trerotola
7,122,017 B2 10/2006 Moutafis et al.
7,220,269 B1 5/2007 Ansel et al.
7,232,452 B2 6/2007 Adams et al.
7,374,560 B2 5/2008 Ressemann et al.
7,431,711 B2 10/2008 Moutafis et al.
7,479,147 B2 1/2009 Honeycutt et al.
7,481,222 B2 1/2009 Reissmann

(56) References Cited

U.S. PATENT DOCUMENTS 7,588,033 B2 9/2009 Wondka
7,591,816 B2 9/2009 Wang et al.
7,604,612 B2 10/2009 Ressemann et al.
7,615,042 B2 11/2009 Beyar et al.
7,621,886 B2 11/2009 Burnett
7,654,996 B2 2/2010 Lynn
7,655,016 B2 2/2010 Demarais et al.
7,666,161 B2 2/2010 Nash et al.
7,699,804 B2 4/2010 Barry et al.
7,713,235 B2 5/2010 Torrance et al.
7,717,685 B2 5/2010 Moutafis et al.
7,717,898 B2 5/2010 Gately et al.
7,736,355 B2 6/2010 Itou et al.
7,753,868 B2 7/2010 Hoffa
7,753,880 B2 7/2010 Malackowski
7,766,894 B2 8/2010 Weitzner et al.
7,776,005 B2 8/2010 Haggstrom et al.
7,798,996 B1 9/2010 Haddad et al.
7,798,999 B2 9/2010 Bailey et al.
7,806,864 B2 10/2010 Haddad et al.
7,833,239 B2 11/2010 Nash
7,842,055 B2 11/2010 Pintor et al.
7,846,175 B2 12/2010 Bonnette et al.
7,862,575 B2 1/2011 Tal
7,867,192 B2 1/2011 Bowman et al.
7,875,004 B2 1/2011 Yodfat et al.
7,879,022 B2 2/2011 Bonnette et al.
7,887,510 B2 2/2011 Karpowicz et al.
7,905,710 B2 3/2011 Wang et al.
7,909,801 B2 3/2011 Hinchliffe
7,909,810 B2 3/2011 Noone
7,914,482 B2 3/2011 Urich et al.
7,914,549 B2 3/2011 Morsi
7,918,654 B2 4/2011 Mahan
7,918,822 B2 4/2011 Kumar et al.
7,918,835 B2 4/2011 Callahan et al.
7,935,077 B2 5/2011 Thor et al.
7,951,073 B2 5/2011 Freed
7,951,107 B2 5/2011 Staid et al.
7,951,112 B2 5/2011 Patzer
7,959,603 B2 6/2011 Wahr et al.
7,959,608 B2 6/2011 Nash et al.
7,976,528 B2 7/2011 Nash et al.
7,981,128 B2 7/2011 To et al.
7,981,129 B2 7/2011 Nash et al.
3,007,490 A1 8/2011 Schaeffer et al.
7,998,114 B2 8/2011 Lombardi
3,012,766 A1 9/2011 Graham
8,021,351 B2 9/2011 Boldenow et al.
3,034,018 A1 10/2011 Lutwyche
8,043,312 B2 10/2011 Noriega et al.
8,043,313 B2 10/2011 Krolik et al.
8,062,246 B2 11/2011 Moutafis et al.
8,062,257 B2 11/2011 Moberg et al.
8,065,096 B2 11/2011 Moberg et al.
8,066,677 B2 11/2011 Lunn et al.
8,070,694 B2 12/2011 Galdonik et al.
8,075,546 B2 12/2011 Carlisle et al.
8,092,483 B2 1/2012 Galdonik et al.
8,123,777 B2 2/2012 Krolik et al.
8,140,146 B2 3/2012 Kim et al.
8,142,458 B2 3/2012 Shturman
8,152,782 B2 4/2012 Jang et al.
8,152,951 B2 4/2012 Zawacki et al.
8,157,787 B2 4/2012 Nash et al.
8,162,877 B2 4/2012 Bonnette et al.
8,162,966 B2 4/2012 Connor et al.
8,177,739 B2 5/2012 Cartledge et al.
8,182,462 B2 5/2012 Istoc et al.
8,187,228 B2 5/2012 Bikovsky
8,187,229 B2 5/2012 Weitzner et al.
8,202,243 B2 6/2012 Morgan
8,209,060 B2 6/2012 Ledford
8,221,348 B2 7/2012 Hackett et al.
8,226,673 B2 7/2012 Nash et al.
8,246,573 B2 8/2012 Ali et al.
8,246,580 B2 8/2012 Hopkins et al.
8,257,298 B2 9/2012 Hamboly
8,257,343 B2 9/2012 Chan et al.
8,262,645 B2 9/2012 Bagwell et al.
8,267,893 B2 9/2012 Moberg et al.
8,287,485 B2 10/2012 Kimura et al.
8,291,337 B2 10/2012 Gannin et al.
8,292,841 B2 10/2012 Gregersen
8,308,745 B2 11/2012 Seto et al.
8,317,739 B2 11/2012 Kuebler
8,317,770 B2 11/2012 Miesel et al.
8,317,773 B2 11/2012 Appling et al.
8,317,786 B2 11/2012 Dahla et al.
8,323,239 B2 12/2012 Bednarek et al.
8,323,268 B2 12/2012 Ring et al.
8,337,175 B2 12/2012 Dion et al.
8,337,451 B2 12/2012 Lareau et al.
8,343,097 B2 1/2013 Pile-Spellman et al.
8,343,131 B2 1/2013 Vinten-Johansen
8,348,896 B2 1/2013 Wagner
8,353,858 B2 1/2013 Kozak et al.
8,353,860 B2 1/2013 Boulais et al.
8,357,138 B2 1/2013 Pierpont et al.
8,372,038 B2 2/2013 Urich et al.
8,394,078 B2 3/2013 Torrance et al.
8,398,579 B2 3/2013 Morris et al.
8,398,581 B2 3/2013 Panotopoulos
8,398,582 B2 3/2013 Gordon et al.
8,414,521 B2 4/2013 Baker et al.
8,414,522 B2 4/2013 Kamen et al.
8,414,943 B2 4/2013 McGuckin, Jr. et al.
8,419,709 B2 4/2013 Haddad et al.
8,425,458 B2 4/2013 Scopton
8,430,837 B2 4/2013 Jenson et al.
8,430,845 B2 4/2013 Wahr et al.
8,430,861 B2 4/2013 Schwartz et al.
8,439,876 B2 5/2013 Spohn et al.
8,454,557 B1 6/2013 Qi et al.
8,465,456 B2 6/2013 Stivland
8,465,867 B2 6/2013 Kim
8,483,980 B2 7/2013 Moberg et al.
8,491,523 B2 7/2013 Thor et al.
8,500,697 B2 8/2013 Kurth et al.
8,506,537 B2 8/2013 Forstensen et al.
8,523,801 B2 9/2013 Nash et al.
8,529,498 B2 9/2013 Moutafis et al.
8,545,432 B2 10/2013 Renati et al.
8,545,514 B2 10/2013 Ferrera
8,562,555 B2 10/2013 MacMahon et al.
8,579,926 B2 11/2013 Pintor et al.
8,597,238 B2 12/2013 Bonnette et al.
8,608,699 B2 12/2013 Blomquist
8,613,618 B2 12/2013 Brokx
8,613,724 B2 12/2013 Lanier, Jr. et al.
8,617,110 B2 12/2013 Moberg et al.
8,617,127 B2 12/2013 Woolston et al.
8,623,039 B2 1/2014 Seto et al.
8,628,549 B2 1/2014 To et al.
8,641,671 B2 2/2014 Michaud et al.
8,647,294 B2 2/2014 Bonnette et al.
8,652,086 B2 2/2014 Gerg et al.
8,657,777 B2 2/2014 Kozak et al.
8,657,785 B2 2/2014 Torrance et al.
8,663,259 B2 3/2014 Levine et al.
8,668,464 B2 3/2014 Kensy et al.
8,668,665 B2 3/2014 Gerg et al.
8,670,836 B2 3/2014 Aeschlimann et al.
8,672,876 B2 3/2014 Jacobson et al.
8,681,010 B2 3/2014 Moberg et al.
8,715,237 B2 5/2014 Moberg et al.
8,721,674 B2 5/2014 Kusleika
8,758,325 B2 6/2014 Webster et al.
8,758,364 B2 6/2014 Eckhouse et al.
8,783,151 B1 6/2014 Janardhan et al.
8,803,030 B1 8/2014 Janardhan et al.
8,814,892 B2 8/2014 Galdonik et al.
8,851,866 B2 10/2014 Moutafis et al.
8,852,219 B2 10/2014 Wulfman et al.

(56) References Cited

U.S. PATENT DOCUMENTS

| | | | |
|---|---|---|---|
| 8,864,792 | B2 | 10/2014 | Eckhouse et al. |
| 8,888,801 | B2 | 11/2014 | To et al. |
| 8,900,179 | B2 | 12/2014 | Jenson et al. |
| 8,900,214 | B2 | 12/2014 | Nance et al. |
| 8,920,402 | B2 | 12/2014 | Nash et al. |
| 8,932,320 | B1 | 1/2015 | Janardhan et al. |
| 8,932,321 | B1 | 1/2015 | Janardhan et al. |
| 8,936,447 | B2 | 1/2015 | Abal |
| 8,945,030 | B2 | 2/2015 | Weston |
| 8,962,561 | B2 | 2/2015 | Shalgi et al. |
| 8,970,384 | B2 | 3/2015 | Yodfat et al. |
| 8,974,418 | B2 | 3/2015 | Bonnette et al. |
| 8,979,798 | B2 | 3/2015 | Shener et al. |
| 8,986,241 | B2 | 3/2015 | Evans et al. |
| 8,986,252 | B2 | 3/2015 | Cummings et al. |
| 8,998,843 | B2 | 4/2015 | Bonnette et al. |
| 9,005,237 | B2 | 4/2015 | Eckhouse et al. |
| 9,011,114 | B2 | 4/2015 | Farrell et al. |
| 9,017,294 | B2 | 4/2015 | McGuckin et al. |
| 9,023,070 | B2 | 5/2015 | Levine et al. |
| 9,024,768 | B2 | 5/2015 | Mandro et al. |
| 9,033,925 | B2 | 5/2015 | Moberg et al. |
| 9,034,008 | B2 | 5/2015 | Eckhouse et al. |
| 9,042,938 | B2 | 5/2015 | Nimbalker et al. |
| 9,078,691 | B2 | 7/2015 | Morris et al. |
| 9,113,955 | B2 | 8/2015 | Noriega et al. |
| 9,119,941 | B2 | 9/2015 | Rollins et al. |
| 9,119,942 | B1 | 9/2015 | Rollins et al. |
| 9,198,679 | B2 | 12/2015 | To et al. |
| 9,238,122 | B2 | 1/2016 | Malhi et al. |
| 9,248,221 | B2 | 2/2016 | Look et al. |
| 9,254,144 | B2 | 2/2016 | Nguyen et al. |
| 9,278,189 | B2 | 3/2016 | Corbett |
| 9,282,992 | B2 | 3/2016 | Levine et al. |
| 9,283,040 | B2 | 3/2016 | Hendrick et al. |
| 9,308,016 | B2 | 4/2016 | Escudero et al. |
| 9,314,263 | B2 | 4/2016 | Escudero et al. |
| 9,332,999 | B2 | 5/2016 | Ray et al. |
| 9,333,007 | B2 | 5/2016 | Escudero et al. |
| 9,358,035 | B2 | 6/2016 | Kojima |
| 9,402,938 | B2 | 8/2016 | Aklog et al. |
| 9,433,427 | B2 | 9/2016 | Look et al. |
| 9,456,872 | B2 | 10/2016 | Hendrick et al. |
| 9,474,543 | B2 | 10/2016 | McGuckin et al. |
| 9,492,192 | B2 | 11/2016 | To et al. |
| 9,492,193 | B2 | 11/2016 | To et al. |
| 9,510,854 | B2 | 12/2016 | Mallaby |
| 9,586,023 | B2 | 3/2017 | Bonnette et al. |
| 9,592,073 | B2 | 3/2017 | Kojima et al. |
| 9,597,480 | B2 | 3/2017 | Purdy et al. |
| 9,693,789 | B2 | 7/2017 | Garrison et al. |
| 9,700,346 | B2 | 7/2017 | Levine et al. |
| 9,770,551 | B1 | 9/2017 | Faden |
| 9,782,195 | B2 | 10/2017 | Mactaggart et al. |
| 9,795,406 | B2 | 10/2017 | Levine et al. |
| 9,808,266 | B2 | 11/2017 | Ray et al. |
| 9,827,404 | B2 | 11/2017 | Nance et al. |
| 9,833,257 | B2 | 12/2017 | Bonnette et al. |
| 9,883,877 | B2 | 2/2018 | Look et al. |
| 10,238,853 | B2 | 3/2019 | Kume et al. |
| 10,314,608 | B2 | 6/2019 | Jenson et al. |
| 10,383,983 | B2 | 8/2019 | Aklog et al. |
| 10,390,926 | B2 | 8/2019 | Janardhan et al. |
| 10,426,885 | B2 | 10/2019 | Criado et al. |
| 10,499,944 | B2 | 12/2019 | Mallaby |
| 10,531,883 | B1 | 1/2020 | Deville et al. |
| 10,702,292 | B2 | 7/2020 | Look et al. |
| 10,716,880 | B2 | 7/2020 | Culbert et al. |
| 2001/0004700 | A1 | 6/2001 | Honeycutt et al. |
| 2001/0051811 | A1 | 12/2001 | Bonnette et al. |
| 2002/0016564 | A1 | 2/2002 | Courtney et al. |
| 2002/0029052 | A1 | 3/2002 | Evans et al. |
| 2002/0058904 | A1 | 5/2002 | Boock et al. |
| 2002/0068895 | A1 | 6/2002 | Beck |
| 2002/0133114 | A1 | 9/2002 | Itoh et al. |
| 2002/0138095 | A1 | 9/2002 | Mazzocchi et al. |
| 2002/0165575 | A1 | 11/2002 | Saleh |
| 2002/0173819 | A1 | 11/2002 | Leeflang et al. |
| 2002/0176788 | A1 | 11/2002 | Moutafis et al. |
| 2002/0177789 | A1 | 11/2002 | Ferry et al. |
| 2003/0032918 | A1 | 2/2003 | Quinn |
| 2003/0040694 | A1 | 2/2003 | Dorros et al. |
| 2003/0055404 | A1 | 3/2003 | Moutafis |
| 2003/0069549 | A1 | 4/2003 | MacMahon et al. |
| 2003/0083681 | A1 | 5/2003 | Moutafis et al. |
| 2003/0088187 | A1 | 5/2003 | Saadat et al. |
| 2003/0088209 | A1 | 5/2003 | Chiu et al. |
| 2003/0139751 | A1 | 7/2003 | Evans et al. |
| 2003/0144688 | A1 | 7/2003 | Brady et al. |
| 2003/0216760 | A1* | 11/2003 | Welch ............ A61B 17/320758 606/159 |
| 2003/0220556 | A1 | 11/2003 | Porat et al. |
| 2003/0236533 | A1 | 12/2003 | Wilson et al. |
| 2004/0030281 | A1 | 2/2004 | Goble et al. |
| 2004/0049149 | A1 | 3/2004 | Drasler et al. |
| 2004/0049225 | A1 | 3/2004 | Denison |
| 2004/0054322 | A1 | 3/2004 | Vargas |
| 2004/0082915 | A1 | 4/2004 | Kadan |
| 2004/0087988 | A1* | 5/2004 | Heitzmann .... A61B 17/320758 606/159 |
| 2004/0097829 | A1 | 5/2004 | McRury et al. |
| 2004/0143225 | A1 | 7/2004 | Callan et al. |
| 2004/0147871 | A1 | 7/2004 | Burnett |
| 2004/0153109 | A1 | 8/2004 | Tiedtke et al. |
| 2004/0158136 | A1 | 8/2004 | Gough et al. |
| 2004/0167463 | A1 | 8/2004 | Zawacki |
| 2004/0193046 | A1 | 9/2004 | Nash et al. |
| 2004/0199201 | A1 | 10/2004 | Kellet et al. |
| 2004/0215222 | A1 | 10/2004 | krivoruchko |
| 2004/0236214 | A1 | 11/2004 | Opie et al. |
| 2004/0243157 | A1 | 12/2004 | Connor et al. |
| 2005/0004594 | A1 | 1/2005 | Nool et al. |
| 2005/0043682 | A1 | 2/2005 | Kucklick et al. |
| 2005/0049547 | A1 | 3/2005 | Anspach et al. |
| 2005/0065426 | A1 | 3/2005 | Porat et al. |
| 2005/0085769 | A1 | 4/2005 | Macmahon et al. |
| 2005/0102165 | A1 | 5/2005 | Oshita et al. |
| 2005/0159716 | A1 | 7/2005 | Kobayashi et al. |
| 2005/0196748 | A1 | 9/2005 | Ericson |
| 2005/0238503 | A1 | 10/2005 | Rush et al. |
| 2005/0240116 | A1 | 10/2005 | Saadat et al. |
| 2005/0240120 | A1 | 10/2005 | Modesitt |
| 2005/0240146 | A1 | 10/2005 | Nash et al. |
| 2005/0244521 | A1 | 11/2005 | Strickland et al. |
| 2005/0277851 | A1 | 12/2005 | Whittaker et al. |
| 2005/0283150 | A1 | 12/2005 | Moutafis et al. |
| 2006/0009785 | A1 | 1/2006 | Maitland et al. |
| 2006/0041245 | A1 | 2/2006 | Ferry et al. |
| 2006/0058836 | A1 | 3/2006 | Bose et al. |
| 2006/0063973 | A1 | 3/2006 | Makower et al. |
| 2006/0064051 | A1 | 3/2006 | Gross |
| 2006/0064123 | A1 | 3/2006 | Bonnette et al. |
| 2006/0074442 | A1 | 4/2006 | Noriega et al. |
| 2006/0093989 | A1 | 5/2006 | Hahn et al. |
| 2006/0142630 | A1 | 6/2006 | Meretei |
| 2006/0149191 | A1 | 7/2006 | DiFiore |
| 2006/0184186 | A1 | 8/2006 | Noone |
| 2006/0212055 | A1 | 9/2006 | Karabey et al. |
| 2006/0229550 | A1 | 10/2006 | Staid et al. |
| 2006/0229587 | A1 | 10/2006 | Beyar et al. |
| 2006/0264808 | A1 | 11/2006 | Staid et al. |
| 2006/0282150 | A1 | 12/2006 | Olson et al. |
| 2007/0016105 | A1 | 1/2007 | Mamourian |
| 2007/0060879 | A1 | 3/2007 | Weitzner et al. |
| 2007/0073233 | A1 | 3/2007 | Thor et al. |
| 2007/0073268 | A1 | 3/2007 | Goble et al. |
| 2007/0078438 | A1 | 4/2007 | Okada |
| 2007/0118165 | A1 | 5/2007 | DeMello et al. |
| 2007/0135812 | A1 | 6/2007 | Sartor |
| 2007/0167804 | A1 | 7/2007 | Park et al. |
| 2007/0197956 | A1 | 8/2007 | Le et al. |
| 2007/0197963 | A1 | 8/2007 | Griffiths et al. |
| 2007/0219467 | A1 | 9/2007 | Clark et al. |
| 2007/0225615 | A1 | 9/2007 | Chechelski et al. |

(56) References Cited

U.S. PATENT DOCUMENTS

| | | | |
|---|---|---|---|
| 2007/0225739 A1 | 9/2007 | Pintor et al. | |
| 2007/0239182 A1 | 10/2007 | Glines et al. | |
| 2007/0249990 A1 | 10/2007 | Cosmescu | |
| 2007/0270755 A1 | 11/2007 | Von et al. | |
| 2007/0299306 A1 | 12/2007 | Parasher et al. | |
| 2008/0009784 A1 | 1/2008 | Leedle et al. | |
| 2008/0091061 A1 | 4/2008 | Kumar et al. | |
| 2008/0097339 A1 | 4/2008 | Ranchod et al. | |
| 2008/0097465 A1* | 4/2008 | Rollins | A61M 25/09041 606/108 |
| 2008/0097563 A1 | 4/2008 | Petrie et al. | |
| 2008/0108960 A1 | 5/2008 | Shapland et al. | |
| 2008/0119824 A1 | 5/2008 | Weitzner et al. | |
| 2008/0125698 A1 | 5/2008 | Gerg et al. | |
| 2008/0125798 A1 | 5/2008 | Osborne et al. | |
| 2008/0195058 A1 | 8/2008 | Moutafis et al. | |
| 2008/0195139 A1 | 8/2008 | Donald et al. | |
| 2008/0243054 A1 | 10/2008 | Mollstam et al. | |
| 2008/0243153 A1 | 10/2008 | Nguyen et al. | |
| 2008/0249501 A1 | 10/2008 | Yamasaki | |
| 2008/0255539 A1 | 10/2008 | Booth | |
| 2008/0255596 A1 | 10/2008 | Jenson et al. | |
| 2008/0294008 A1 | 11/2008 | Toyama | |
| 2008/0294181 A1 | 11/2008 | Wensel et al. | |
| 2008/0306465 A1 | 12/2008 | Bailey et al. | |
| 2008/0319376 A1 | 12/2008 | Wilcox et al. | |
| 2009/0018566 A1* | 1/2009 | Escudero | A61M 25/0138 606/159 |
| 2009/0048607 A1 | 2/2009 | Rockley | |
| 2009/0054825 A1 | 2/2009 | Melsheimer et al. | |
| 2009/0082722 A1 | 3/2009 | Munger et al. | |
| 2009/0105645 A1 | 4/2009 | Kidd et al. | |
| 2009/0105690 A1 | 4/2009 | Schaeffer et al. | |
| 2009/0157057 A1 | 6/2009 | Ferren et al. | |
| 2009/0264940 A1 | 10/2009 | Beale et al. | |
| 2009/0292212 A1 | 11/2009 | Ferren et al. | |
| 2009/0306476 A1 | 12/2009 | Banik et al. | |
| 2009/0306692 A1 | 12/2009 | Barrington et al. | |
| 2010/0010524 A1 | 1/2010 | Barrington et al. | |
| 2010/0030134 A1 | 2/2010 | Fitzgerald et al. | |
| 2010/0030186 A1 | 2/2010 | Stivland | |
| 2010/0094201 A1 | 4/2010 | Mallaby | |
| 2010/0145302 A1 | 6/2010 | Cull et al. | |
| 2010/0160851 A1 | 6/2010 | Dimalanta et al. | |
| 2010/0174233 A1 | 7/2010 | Kuban et al. | |
| 2010/0191178 A1 | 7/2010 | Ross et al. | |
| 2010/0204613 A1 | 8/2010 | Rollins et al. | |
| 2010/0204672 A1 | 8/2010 | Lockhart et al. | |
| 2010/0217275 A1 | 8/2010 | Carmeli et al. | |
| 2010/0217276 A1 | 8/2010 | Garrison et al. | |
| 2010/0228273 A1 | 9/2010 | Staid et al. | |
| 2010/0268236 A1 | 10/2010 | Moutafis et al. | |
| 2010/0274191 A1 | 10/2010 | Ting | |
| 2010/0280534 A1 | 11/2010 | Sher | |
| 2011/0034986 A1 | 2/2011 | Chou et al. | |
| 2011/0091331 A1 | 4/2011 | Moutafis et al. | |
| 2011/0092892 A1 | 4/2011 | Nitsan et al. | |
| 2011/0106019 A1 | 5/2011 | Bagwell et al. | |
| 2011/0152920 A1 | 6/2011 | Eckhouse et al. | |
| 2011/0160683 A1 | 6/2011 | Pinotti Barbosa et al. | |
| 2011/0282426 A1 | 11/2011 | Mitra et al. | |
| 2012/0059340 A1 | 3/2012 | Larsson | |
| 2012/0059354 A1 | 3/2012 | Zarate | |
| 2012/0065656 A1 | 3/2012 | Karwei | |
| 2012/0065660 A1 | 3/2012 | Ferrera et al. | |
| 2012/0071907 A1 | 3/2012 | Pintor et al. | |
| 2012/0078080 A1 | 3/2012 | Foley et al. | |
| 2012/0123509 A1 | 5/2012 | Merrill et al. | |
| 2012/0130415 A1 | 5/2012 | Tal et al. | |
| 2012/0165756 A1 | 6/2012 | Root et al. | |
| 2012/0239008 A1* | 9/2012 | Fojtik | A61M 25/09 606/1 |
| 2012/0239064 A1 | 9/2012 | Cartier et al. | |
| 2012/0239066 A1 | 9/2012 | Levine et al. | |
| 2012/0259265 A1 | 10/2012 | Salehi et al. | |
| 2012/0277665 A1 | 11/2012 | Tachoire et al. | |
| 2012/0289910 A1 | 11/2012 | Shtul et al. | |
| 2012/0291811 A1 | 11/2012 | Dabney et al. | |
| 2012/0330196 A1 | 12/2012 | Nita | |
| 2013/0085381 A1 | 4/2013 | Comerota et al. | |
| 2013/0184734 A1 | 7/2013 | Morris et al. | |
| 2013/0190701 A1 | 7/2013 | Kim | |
| 2013/0218186 A1 | 8/2013 | Dubois et al. | |
| 2013/0245543 A1 | 9/2013 | Gerg et al. | |
| 2013/0267891 A1 | 10/2013 | Malhi et al. | |
| 2013/0281788 A1 | 10/2013 | Garrison | |
| 2013/0310809 A1 | 11/2013 | Armstrong et al. | |
| 2013/0310845 A1 | 11/2013 | Thor et al. | |
| 2013/0331776 A1 | 12/2013 | Klein et al. | |
| 2014/0005699 A1 | 1/2014 | Bonnette et al. | |
| 2014/0058361 A1 | 2/2014 | Gordon | |
| 2014/0142594 A1 | 5/2014 | Fojtik | |
| 2014/0147246 A1 | 5/2014 | Chappel et al. | |
| 2014/0148830 A1 | 5/2014 | Bowman | |
| 2014/0155931 A1 | 6/2014 | Bose et al. | |
| 2014/0228569 A1 | 8/2014 | Okumura et al. | |
| 2014/0228869 A1 | 8/2014 | Bonnette et al. | |
| 2014/0276920 A1 | 9/2014 | Hendrick et al. | |
| 2014/0309589 A1 | 10/2014 | Momose et al. | |
| 2014/0323906 A1 | 10/2014 | Peatfield et al. | |
| 2014/0360494 A1 | 12/2014 | Herskovic | |
| 2014/0378951 A1 | 12/2014 | Dye | |
| 2015/0025446 A1 | 1/2015 | Jacobson et al. | |
| 2015/0032138 A1 | 1/2015 | Jenson et al. | |
| 2015/0094673 A1 | 4/2015 | Pratt et al. | |
| 2015/0094748 A1 | 4/2015 | Nash et al. | |
| 2015/0142030 A1 | 5/2015 | Mactaggart et al. | |
| 2015/0257724 A1 | 9/2015 | Lautenschläger | |
| 2015/0305765 A1* | 10/2015 | Fojtik | A61B 17/32002 606/113 |
| 2015/0327875 A1 | 11/2015 | Look et al. | |
| 2015/0374391 A1 | 12/2015 | Quick et al. | |
| 2016/0051323 A1 | 2/2016 | Stigall et al. | |
| 2016/0058614 A1 | 3/2016 | Ross et al. | |
| 2016/0143721 A1 | 5/2016 | Rosenbluth et al. | |
| 2016/0220741 A1 | 8/2016 | Garrison et al. | |
| 2017/0065396 A1 | 3/2017 | Look et al. | |
| 2017/0079672 A1 | 3/2017 | Quick | |
| 2017/0105745 A1 | 4/2017 | Rosenbluth et al. | |
| 2017/0172603 A1 | 6/2017 | Bonnette et al. | |
| 2017/0181760 A1 | 6/2017 | Look et al. | |
| 2017/0265885 A1 | 9/2017 | Bonnette et al. | |
| 2017/0281204 A1 | 10/2017 | Garrison et al. | |
| 2017/0290598 A1 | 10/2017 | Culbert et al. | |
| 2018/0207397 A1 | 7/2018 | Look et al. | |
| 2018/0214172 A1 | 8/2018 | Donnelly et al. | |
| 2018/0338770 A1 | 11/2018 | Mogi et al. | |
| 2020/0345904 A1 | 11/2020 | Casey et al. | |
| 2020/0367917 A1 | 11/2020 | Teigen et al. | |

FOREIGN PATENT DOCUMENTS

| | | | |
|---|---|---|---|
| CN | 201603160 | U | 10/2010 |
| CN | 103767760 | A | 5/2014 |
| DE | 3715418 | A1 | 11/1987 |
| DE | 4018736 | A1 | 1/1992 |
| EP | 0709110 | A1 | 5/1996 |
| EP | 806213 | A1 | 11/1997 |
| EP | 1092396 | A2 | 4/2001 |
| EP | 726466 | B1 | 4/2002 |
| EP | 1488748 | A1 | 12/2004 |
| EP | 2301450 | B1 | 11/2011 |
| EP | 2859902 | A1 | 4/2015 |
| EP | 2131759 | B1 | 10/2017 |
| JP | 06-125915 | A | 5/1994 |
| JP | 06-205784 | A | 7/1994 |
| JP | 06-205785 | A | 7/1994 |
| JP | 07-299078 | A | 11/1995 |
| JP | 2001-161700 | A | 6/2001 |
| JP | 2003-010194 | A | 1/2003 |
| JP | 2003-101194 | A | 4/2003 |
| JP | 2003-514632 | A | 4/2003 |
| JP | 2003260127 | A | 9/2003 |
| JP | 2003-290236 | A | 10/2003 |

(56) References Cited

FOREIGN PATENT DOCUMENTS

| | | | |
|---|---|---|---|
| JP | 2004-514466 | A | 5/2004 |
| JP | 2007-160109 | A | 6/2007 |
| JP | 2009-039216 | A | 2/2009 |
| JP | 2013-154171 | A | 8/2013 |
| JP | 2013-180156 | A | 9/2013 |
| WO | WO199005493 | A1 | 5/1990 |
| WO | WO1996001079 | A1 | 1/1996 |
| WO | WO1996035469 | A1 | 11/1996 |
| WO | 99/01079 | A1 | 1/1999 |
| WO | WO199918850 | A1 | 4/1999 |
| WO | 00/69348 | A1 | 11/2000 |
| WO | WO2001037916 | A1 | 5/2001 |
| WO | 02/19928 | A2 | 3/2002 |
| WO | WO 02/26289 | A1 | 4/2002 |
| WO | WO2004100772 | A2 | 11/2004 |
| WO | WO 2005/004968 | A1 | 1/2005 |
| WO | WO 2006/081238 | A2 | 8/2006 |
| WO | 2007/087404 | A2 | 8/2007 |
| WO | WO2007143633 | A2 | 12/2007 |
| WO | WO2008097993 | A2 | 8/2008 |
| WO | 2008/121481 | A1 | 10/2008 |
| WO | 2010/023617 | A1 | 3/2010 |
| WO | WO 2010/023671 | A2 | 3/2010 |
| WO | 2015/179329 | A1 | 11/2015 |
| WO | 2016/126974 | A1 | 8/2016 |
| WO | WO2017/112922 | A1 | 6/2017 |
| WO | 2018/215840 | A1 | 11/2018 |

OTHER PUBLICATIONS

Extended European Search Report dated Aug. 31, 2018, in EP App. No 16843162.5 filed Sep. 2, 2016 (10 pages).

JP2003260127A (Machine Translation, Sep. 7, 2018) (5 pages).

"Comparison of Dimensions and Aspiration Rate of the Pronto V3, Pronto LP, Export XT, Export AP, Fetch, Xtract, Diver C.E. and QuickCat Catheter", Vascular Solutions, Inc., downloaded from internet Oct. 22, 2014.

Frölich, G., Meier, P., White, S., Yellon, D., Hausenloy, D., "Myocardial reperfusion injury: looking beyond primary PCI", European Heart Journal Jun. 2013, pp. 1714-1722, vol. 34, No. 23, Elsevier, Amsterdam, The Netherlands.

Gousios, A., Shearn, M, "Effect of Intravenous Heparin on Human Blood Viscosity", Circulation, Dec. 1959, pp. 1063-1066, vol. 20, American Heart Association, Dallas, USA.

"Infusion Liquid Flow Sensors—Safe, Precise and Reliable", Sensirion, downloaded from internet Apr. 3, 2015.

Parikh, A., Ali, F., "Novel Use of GuideLiner Catheter to Perform Aspiration Thrombectomy in a Saphenous Vein Graft" Cath Lab Digest, Oct. 2013, downloaded from internet Oct. 22, 2014.

Prasad, A., Stone, G., Holmes, D., Gersh, B., Peperfusion Injury, Microvascular Dysfunction, and Carioprotection: The "Dark Side" of Reperfusion, Circulation, Nov. 24, 2009, pp. 2105-2112, vol. 120, American Heart Association, Dallas, USA.

Rodriquez, R., Condé-Green, A., "Quantification of Negative Pressures Generated by Syringes of Different Calibers Used for Liposuction", Plastic & Reconstructive Surgery, Aug. 2012, pp. 383e-384e, vol. 130, No. 2, Lippicott Williams & Wilkins, Philadelphia, USA.

Stys, A., Stys, T., Rajpurohit, N., Khan, M. "A Novel Application of GuideLiner Catheter for Thrombectomy in Acute Myocardial Infarction: A Case Series", Journal of Invasive cardiology, Nov. 2013, pp. 620-624, vol. 25, No. 11, King of Prussia, USA.

Makes event the most difficult intervention A Fast and Smooth Run. GuideLiner brochure. Vascular Solutions, Inc. downloaded from internet Apr. 9, 2015.

Angiojet Ultra Power Pulse Kit Information for Use, Medrad, Inc., downloaded from internet Jan. 23, 2017.

Dalal, J., Sahoo, P., Dhall, A., Kapoor, R., Krishnamurthy, A., Shetty, S., Trivedi, S., Kahali, D., Shah, B., Chockalingam, K., Abdullakutty, J., Shetty, P., Chopra, A., Ray, R., Desai, D., Pachiyappan, Ratnaparkhi, G., Sharma, M., Sambasivam, K. "Role of thrombysis in reperfusion therapy for management of AMI: Indian scenario," Indian Heart Journal, 2013, pp. 566-585, vol. 63, Cardiological Society of India, Bombay, India.

Franetzki, M., "Confusion in the Terminology of Insulin Devices", Diabetes Care, Jan.-Feb. 1982, pp. 74-75, vol. 5, No. 1, American Diabetes Association, Alexandria, USA.

Harvard Health; Normal Body Temperature: Rethinking the normal human body temperature; p. 1; published Apr. 1, 2006; http://www.health.harvard.edu/press.sub.-releases/normal.sub.-body.sub.- --temperature.

Irsigler, K, Kritz, H., Hagmuller, G., Franezki, M., Prestele, K, Thurow, H., Geisen, K., "Long-term Continuous Intraperitoneal Insulin Infusion with an Implanted Remote-Controlled Insulin Infusion Device", Diabetes, Dec. 1981, pp. 1072-1075, vol. 30, No. 12, American Diabetes Association, New York, USA.

Kritz, H., Hagmuller, G, Lovett, R., Irsigler, K., "Implanted Constant Basal Rate Insulin Infusion Devices for Type 1 (Insulin-Dependent) Diabetic Patients", Diabetologia, Aug. 1983, pp. 78-81, vol. 25, No. 2, Springer-Verlag, Berlin, Germany.

Lipinski, M., Lee, R., Gaglia, M., Torguson, R., Garcia-Garcia, H., Pichard, A., Satler, L., Waksman, R. "Comparison of heparin, bivalirudin, and different glycoprotein IIb/IIIa inhibitor regimens for anticoagulation during percutaneous coronary intervention: A network meta-analysis," Cardiovascular Revascularization Medicine, 2016, pp. 535-545, vol. 17, Elsevier, New York, USA.

Metzler, L., "Miniature Sensor Combines with Micropump to Control Drug Delivery", Medical Design Technology, Mar. 2017, pp. 22-23, MDTmag.com, Advantage Business Media, Rockaway, USA.

Micossi, et al., "One-Year Trial of a Remote-Controlled Implantable Insulin Infusion System in Type I Diabetic Patients", The Lancet, Oct. 15, 1988, pp. 866-869, vol. 2, No. 8616, Little, Brown & Co, Boston, USA.

Pechlaner, C., Knapp, E., Wiedermann, C. "Hypersensitivity reactions associated with recombinant tissue-type plasminogen activator and urokinase," Blood Coagulation and Fibrinolysis, 2001, pp. 491-494, vol. 12, Lippincott Williams & Wilkins, Hagerstown, USA.

Principles and Practice of Pharmacology for Anaesthetists, ed. Calvey, T., Williams, N., 2008, pp. 324-327, 5th Edition, Blackwell Publishing, Malden, USA.

Puddu, P., Ianetta, L., Placanica, A., Cuturello, D., Schiariti, M., Manfrini, O., "The role of Glycoprotein IIb/IIIa inhibitors in acute coronary syndromes and the interference with anemia," International Journal of Cardiology, 2016, pp. 1091-1096, vol. 222, Elsevier, Amsterdam, The Netherlands.

Saudek, C., Selam, J-L, Pitt, H., Waxman, K., Rubio, M., Jeandidier, N., Turner, D., Fischell, R., Charles, M., "A Preliminary trial of the Programmable Implantable Medication System for Insulin Delivery", The New England Journal of Medicine, Aug. 31, 1989, pp. 574-579, vol. 321, No. 9, Massachusetts Medical Society, Boston, USA.

Selam, J-L, "Development of Implantable Insulin Pumps: Long is the Road", Diabetic Medicine, Nov. 1988, pp. 724-733, vol. 5, No. 8, Wiley, Chichester, UK.

Van De Werf, F, "The ideal fibrinolytic: can drug design improve clinical results?" European Heart Journal, 1999, pp. 1452-1458, vol. 20, Elsevier, Amsterdam, The Netherlands.

Warmerdam, P., Vanderlick, K., Vandervoort, P., de Smedt, H., Plaisance, S., De Maeyer, M., Collen, D. "Saphylokinase-Specific-Cell-Mediated Immunity in Humans," The Journal of Immunology, 2002, pp. 155-161, vol. 168, Williams & Wilkins Co., Baltimore, USA.

* cited by examiner

SYSTEMS AND METHODS FOR MANIPULATING MEDICAL DEVICES

INCORPORATION BY REFERENCE TO ANY PRIORITY APPLICATIONS

This application is a continuation of U.S. patent application Ser. No. 15/256,488, filed on Sep. 2, 2016, now U.S. Pat. No. 10,561,440, which claims the benefit of priority to U.S. Provisional Application No. 62/214,192, filed on Sep. 3, 2015, and U.S. Provisional Application No. 62/286,429, filed on Jan. 24, 2016, all of which are herein incorporated by reference in their entirety for all purposes. Priority is claimed pursuant to 35 U.S.C. § 120 and 35 U.S.C. § 119.

BACKGROUND OF THE INVENTION

Guidewires and other elongate medical devices are configured to be placed within conduits and cavities of the body. These devices may be manipulated manually to move or track the devices through tortuous, obstructed, or stenosed passageways. Such maneuvers are oftentimes challenging and require skill and experience. At times, it is impossible to successfully move or track the devices to desired target locations within the body.

SUMMARY OF THE INVENTION

In a first embodiment of the present disclosure, a method for treating a patient having thrombus includes providing a manipulation device including a housing configured to be supported by the hand of a user, the housing having a distal end and a proximal end, a drive system disposed within the housing, and configured to rotate a rotation member, an engagement member coupled to the rotation member, and configured to be removably coupled to an elongate medical device to transfer rotational movement of the rotation member to rotational movement of an elongate medical device, an activation member carried by the housing such that it can be operated by at least a portion of the hand of the user when the housing is supported by the hand of the user, and wherein the drive system if configured to apply motive force to the engagement member, securing an elongate member to the engagement member, the elongate member having a distal end configured for introduction into a patient's vasculature, introducing at least the distal end of the elongate member into a blood vessel adjacent a thrombus, operating the activation member to cause at least some rotation of the rotation member, which in turn causes at least some rotation of the distal end of the elongate member at or near the thrombus, and aspirating at least some of the thrombus with an aspiration catheter.

In another embodiment of the present disclosure, system for treating a patient having thrombus includes an aspiration catheter having a distal end, a proximal end, and an aspiration lumen extending between the distal end and the proximal end and configured to be coupled to a vacuum source, an elongate member having a distal end and a proximal end, and configured for placement through the aspiration lumen of the aspiration catheter, a manipulation device including a housing configured to be supported by the hand of a user, the housing having a distal end and a proximal end, a drive system disposed within the housing, and configured to rotate a rotation member, an engagement member coupled to the rotation member, and configured to be removably coupled to the elongate member to transfer rotational movement of the rotation member to rotational movement of the elongate member, an activation member carried by the housing such that it can be operated by at least a portion of the hand of the user when the housing is supported by the hand of the user, and wherein the drive system if configured to apply motive force to the engagement member to thereby move the elongate member.

DETAILED DESCRIPTION OF THE ILLUSTRATED EMBODIMENTS

Embodiments of the present disclosure comprise systems and methods for manipulating one or more medical devices. The medical devices may include elongated medical devices including, but not limited to: guidewires (guide wires), maceration devices, for example maceration devices having an expending element (such as a basket), cutting devices, atherectomy devices, and a variety of different catheter shafts, including solid catheter shafts and hollow catheter shafts. Conventional guidewire manual manipulation methods often involve applying torque to the guidewire to aid its passage through tortuous, occluded, or stenosed conduits or vessels. The user may sometimes spin the guidewire within the fingers (e.g., gloved fingers) to create a torque which assists in manipulating the guidewire through the challenging anatomy. This technique is sometimes referred to as "helicoptering," alluding to the spinning blades of a helicopter. This technique can be difficult to achieve because the typically small diameter of guidewires makes them difficult to grip. Additionally, it may be difficult to apply necessary friction to the surface of the guidewire to cause them to rotate, because guidewires are often covered with a lubricious coating. For similar reasons, it may be difficult to place a longitudinal force on the guidewires with manual manipulation, including a back-and-forth longitudinal force intended for placing an oscillatory motion on the guidewire.

Figure 1:
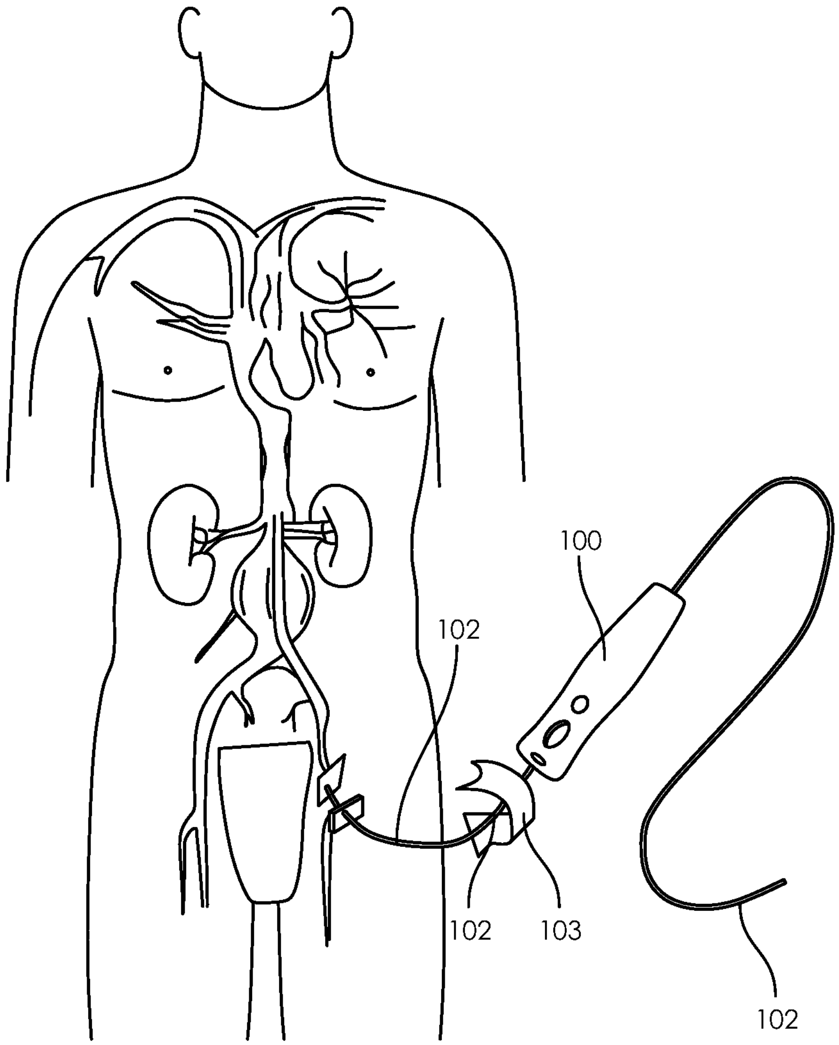
FIG. 1 illustrates a view of a guidewire manipulation device being used on a patient according to an embodiment of the present disclosure.

FIG. 1 illustrates an embodiment of a guidewire manipulation device 100 which is advanced over a guidewire 102. As seen in this figure, the guidewire 102 is introduced into a blood vessel of the patient (e.g., a femoral artery). The manipulation device 100 is slid over the guidewire 102 and selectively locked on to the guidewire 102. As the guidewire 102 is advance into the patient, the user operates the manipulation device 100 to rotate or vibrate the guidewire 102 as appropriate.

For example, as a distal end of the guidewire 102 reaches an angled or curved region of the vessel, the user activates the manipulation device 100 to rotate the guidewire 102 (i.e., in a counter clockwise direction indicated by arrow 103), thereby causing the distal end of the guidewire 102 to more easily advance through the angled or curved region. In another example, the distal end of the guidewire 102 reaches an obstruction (e.g., an embolism) but is unable to easily pass. The user then activates the guidewire manipulation device 100 to vibrate (e.g., by routing between a clockwise and counter clockwise direction quickly), thereby causing the distal end of the guidewire 102 to pass through the obstruction. In another example, the device 100 may include a multiple, preprogrammed rotation patterns appropriate for different vessel configurations (e.g., a 180 degree clockwise rotation followed by 180 degree counter-clockwise rotation, a 90 degree clockwise rotation followed by 90 degree counter clockwise rotation or a 30 degree clockwise rotation followed by 180 degree counter clockwise rotation).

Figure 2A:
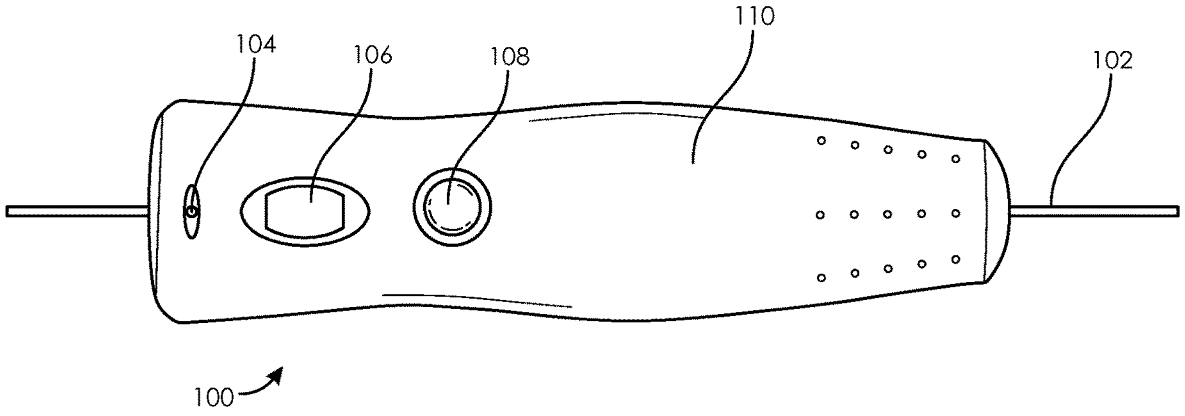
FIG. 2A illustrates a top view of the guidewire manipulation device of FIG. 1.
Figure 2B:
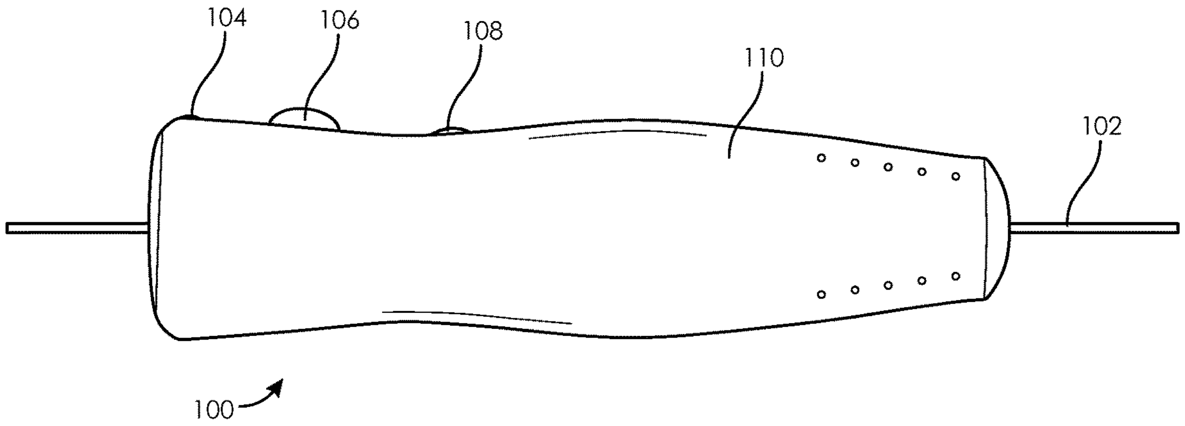
FIG. 2B illustrates a side view of the guidewire manipulation device of FIG. 1.

FIGS. 2A and 2B illustrate external views of the guidewire manipulation device 100. The guidewire manipulation device 100 may also include a microprocessor and memory connected to the motor and a button 108 for storing and executing the preprogrammed rotation patterns. As seen in these figures, the guidewire 102 passes through a passage along the length of the guidewire manipulation device 100. Preferably, the guidewire manipulation device 100 includes a locking assembly in the form of a guidewire lock switch 106 which allows the user to selectively lock the guidewire manipulation device 100 to the guidewire 102. In this respect, the guidewire manipulation device 100 can move relative to the guidewire 102 in an unlocked state, and can move the guidewire 102 (rotationally and/or longitudinally) in a locked state.

The guidewire manipulation device 100 also preferably includes a power indicator light 104 (e.g., an LED) which indicates if the device 100 is powered on and a rotation button 108 which causes the guidewire 102 to rotate. By pressing the button 108, the user activates the device 100. Optionally, the device 100 may include a button, switch or similar mechanism to toggle the device 100 between rotating in a clockwise direction or a counter-clockwise direction. Alternately, the button 108 may include multiple actuation techniques for determining clockwise or counter-clockwise rotation (e.g., sliding forward or backward, multiple button presses, etc.).

Preferably, an outer container or casing 110 is composed of a light-weight material such as plastic and has an ergonomic shape that at least partially fits in the user's hand. In this respect, the user can comfortably operate the guidewire manipulation device 100 during a procedure.

Figure 3:
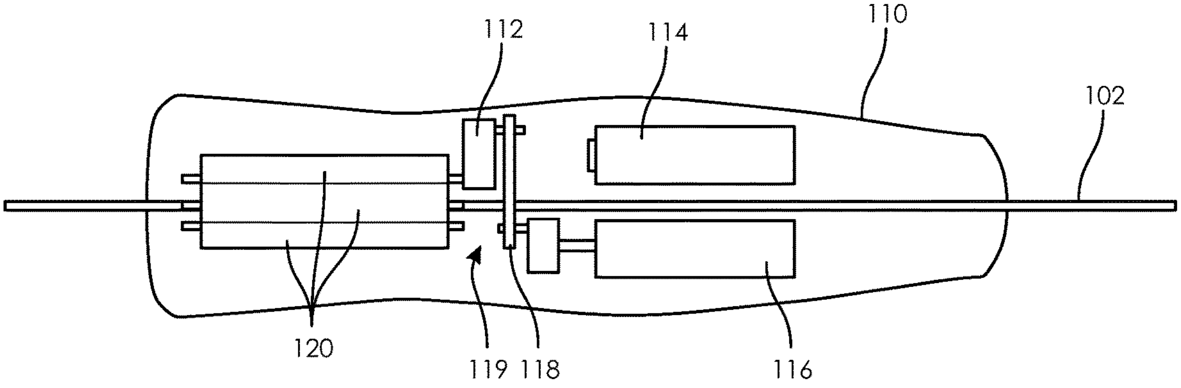
FIG. 3 frustrates a top open view of the guidewire manipulation device of FIG. 1.
Figure 4:
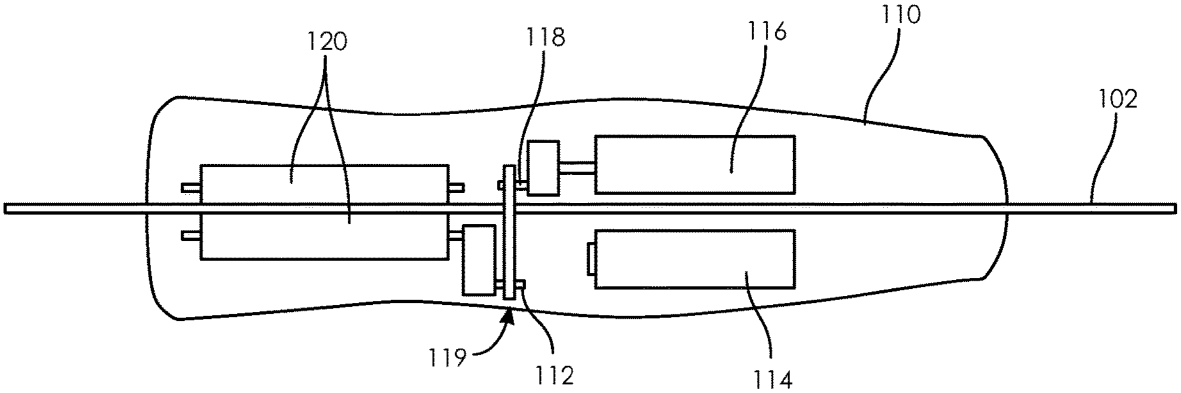
FIG. 4 illustrates a bottom open view of the guidewire manipulation device of FIG. 1.
Figure 5:
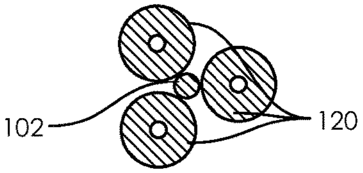
FIG. 5 illustrates a cross sectional view of the rollers of the guidewire manipulation device of FIG. 1.

Referring to FIGS. 3 and 4, an interior view of the guidewire manipulation device 100 within the outer easing 110 is illustrated according to an embodiment of the present disclosure. The guidewire 102 is engaged by the device 100 with elongated rollers 120 (also seen in the cross sectional view of FIG. 5). Preferably the device 100 includes at least three rollers, however, any number of rollers 120 are possible (e.g., 1-5 rollers). When; the button 108 is pressed, the rollers 120 rotate, thereby rotating the guidewire 102. Preferably, the lock switch 106 raises or lowers one or more of the rollers 120 in relation to the guidewire 102, so as to lock the guidewire 102 with the device 100 when the rollers 120 are pressed against the guidewire 102 and unlock the guidewire 102 from the device 100 when the roller(s) 120 are moved away from the guidewire 102.

One or more of the rollers 120 are preferably driven by a motor 116 which is powered by battery 114 (or alternately by A.C. power such as an outlet). The motor 116 connects to the roller(s) 120 by a cam 119 made up of a first linkage 118 connected to the motor 116 and a second linkage 112 connected to the roller(s) 120. In this respect, activation of the motor 116 drives the cam 119 and ultimately rotation of one or more of the rollers 120.

Figure 6:
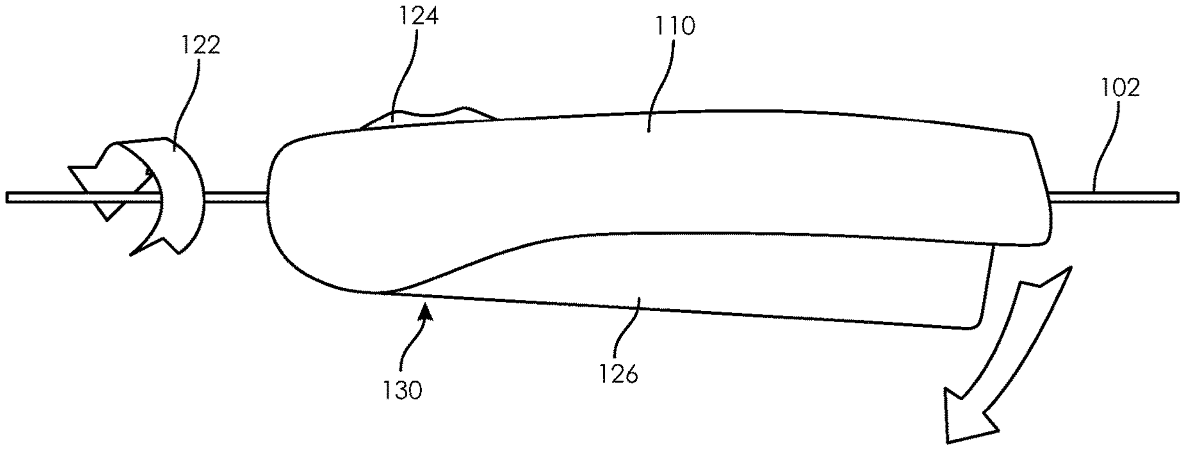
FIG. 6 illustrates a side view of a guidewire manipulation device according to an embodiment of the present disclosure.
Figure 7:
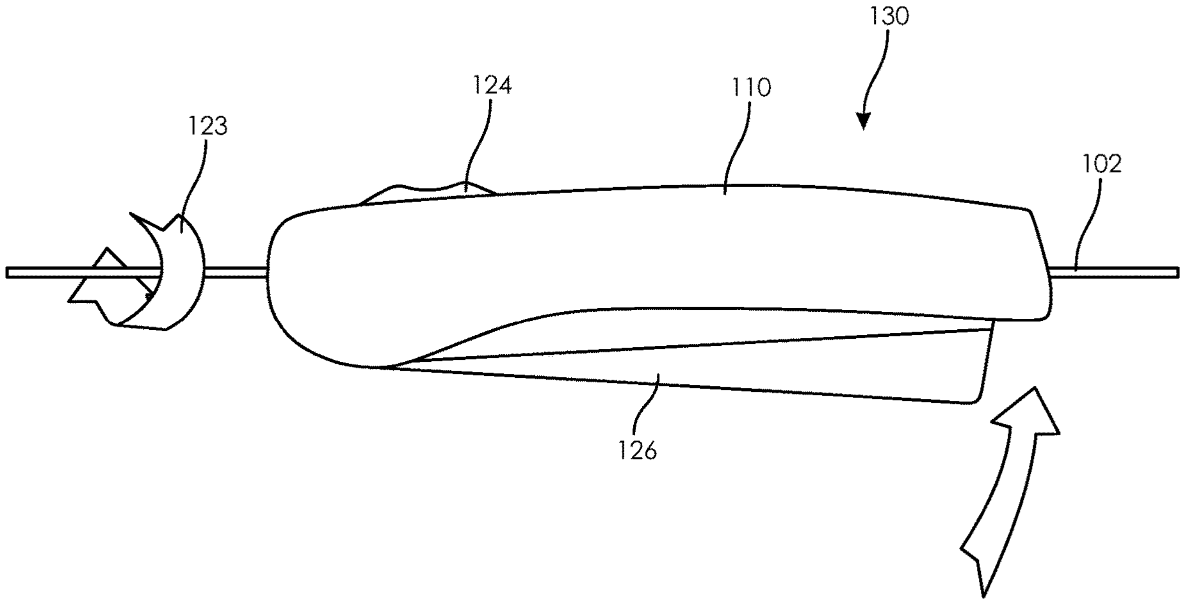
FIG. 7 illustrates a side view of the guidewire manipulation device of FIG. 6 with a depressed trigger according to an embodiment of the present disclosure.

FIGS. 6 and 7 illustrate another embodiment of a manual manipulation device 130 according to the present disclosure. The device 130 is generally similar to the previously described device 100, except that the rollers 120 and therefore rotation at the guidewire 102 is driven by a handle 126. For example, depressing the handle 126 rotates the guidewire 102 in a clockwise direction (arrow 122) and releasing the handle 126 rotates the guidewire 102 in a counter clockwise direction (arrow 123). Additionally, a switch 124 is included to change a type of rotation caused by the handle 126. For example, the switch 124 may change a gear ratio and therefore the amount of rotation cause by depressing the handle. In another example, the switch 124 may change directions of rotation caused by depressing the handle 126. By manual activation of the handle 126 by the user, the internal drive components drive the rotation of the guidewire 102 without the need of a motor 116.

Figure 8:
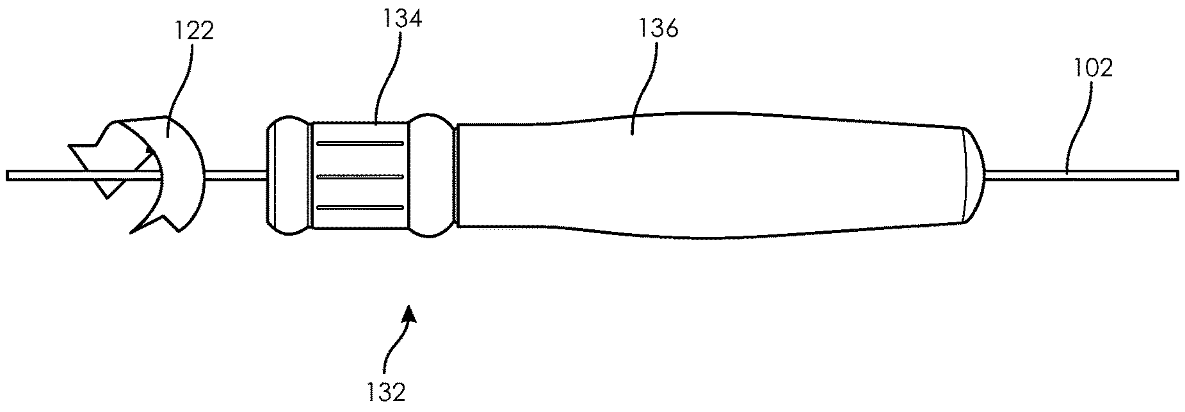
FIG. 8 illustrates a side view of a guidewire manipulation device according to an embodiment of the present disclosure.
Figure 9:
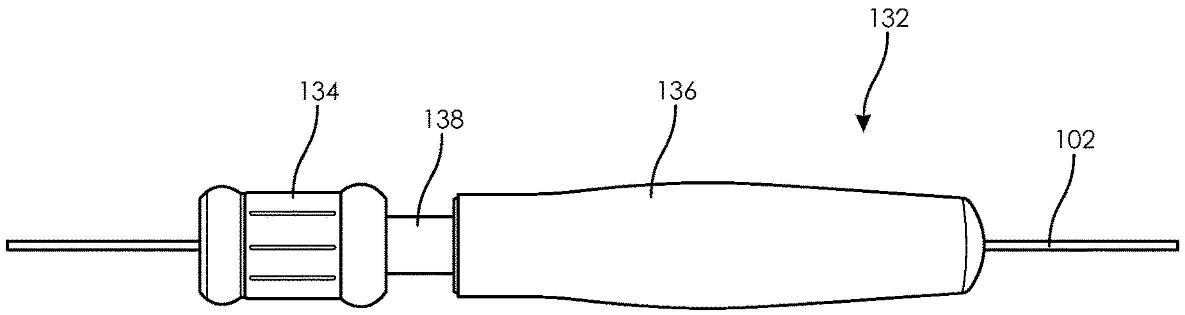
FIG. 9 illustrates a side view of the guide-wire manipulation device of FIG. 8.
Figure 10:
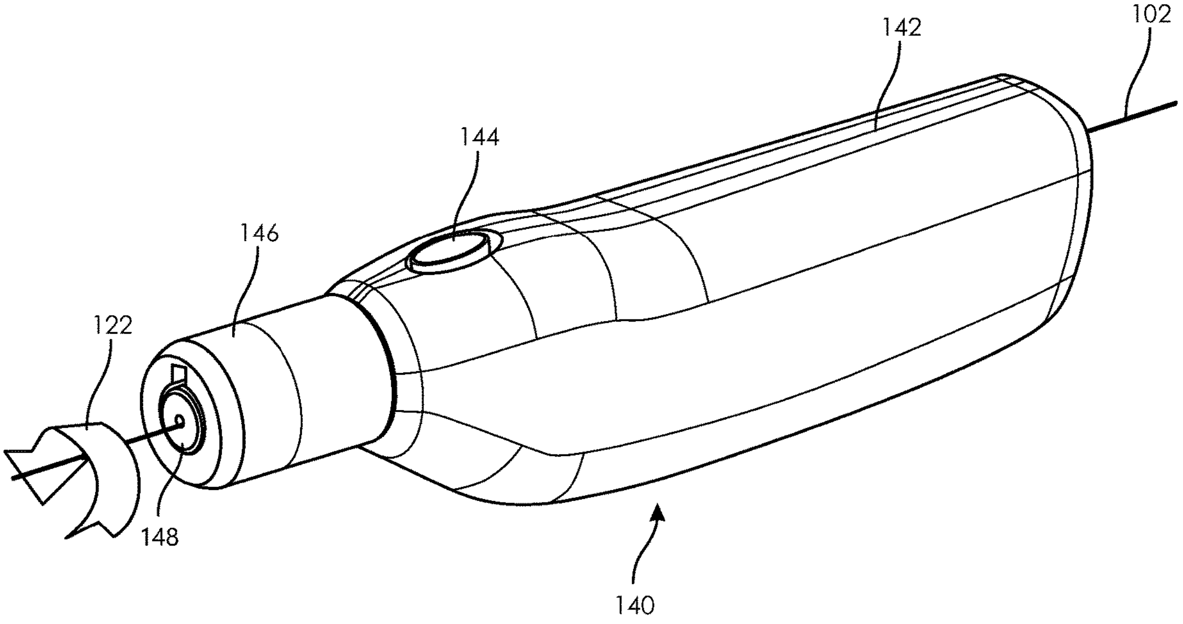
FIG. 10 illustrates a perspective view of a guide-wire manipulation device according to an embodiment of the present disclosure.

FIGS. 8 and 9 illustrate another embodiment of a manual guidewire manipulation device 132 which is generally similar to the previously described devices 100 and 130. However, the device 132 includes a selectively locking thumb roller 134 on a distal end of the device 132. The thumb roller 134 includes a locked mode, seen in FIG. 8, in which the roller 134 is engaged with the guidewire 102, thereby allowing the user to roll the roller 134 and thus the guidewire 102. The thumb roller 134 also includes an unlocked mode, seen in FIG. 9, in which the roller 134 is pulled distally from the casing 136, exposing space 138 and disengaging the roller 134 from the guidewire 102. Thus, in the unlocked mode, the device 132 can be moved along the length of the guidewire 102.

Figure 11:
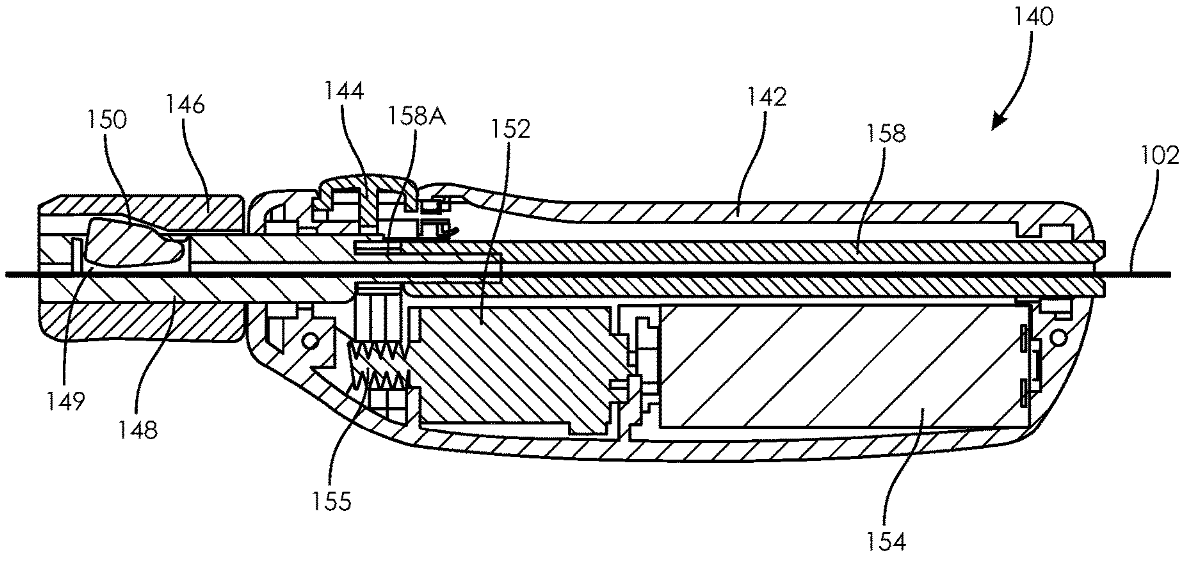
FIG. 11 illustrates a side cross sectional view of the guidewire manipulation device of FIG. 10.
Figure 12:
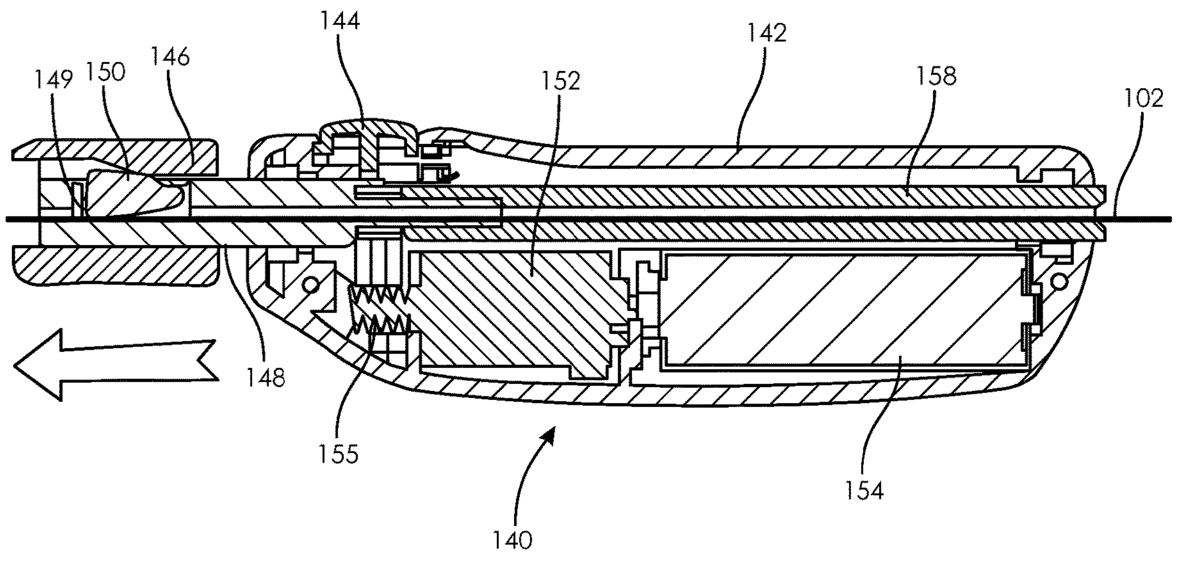
FIG. 12 illustrates a side cross sectional view of the guidewire manipulation device of FIG. 10.
Figure 13:
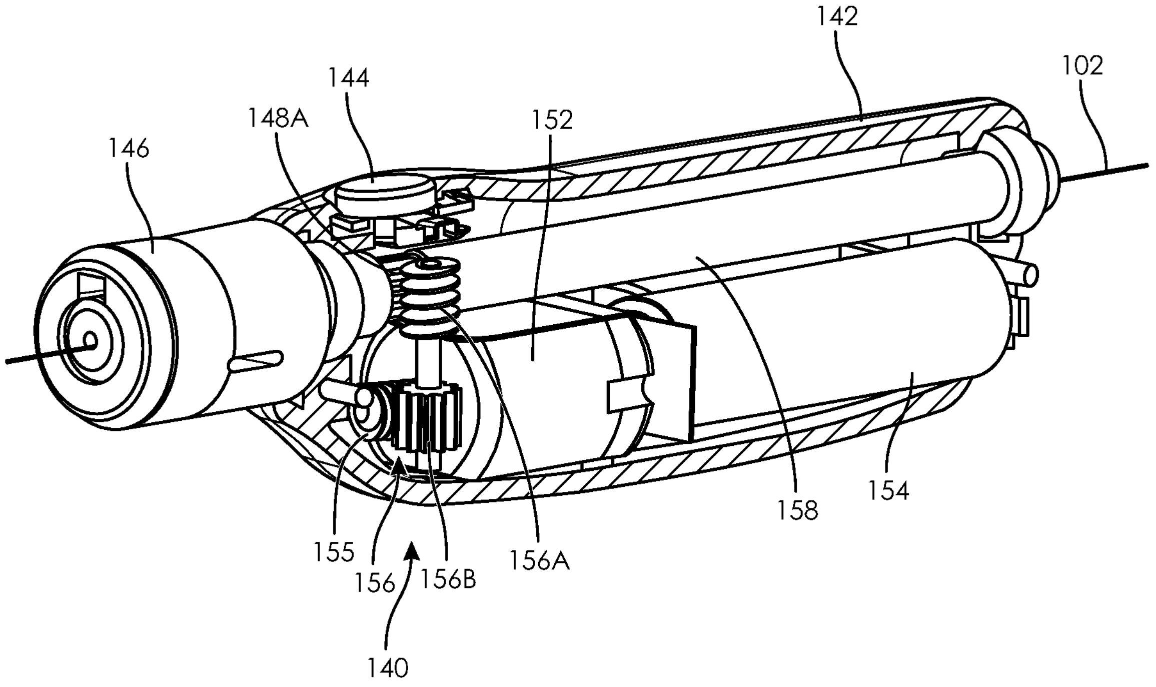
FIG. 13 illustrates a perspective open view of the guidewire manipulation device of FIG. 10.
Figure 14:
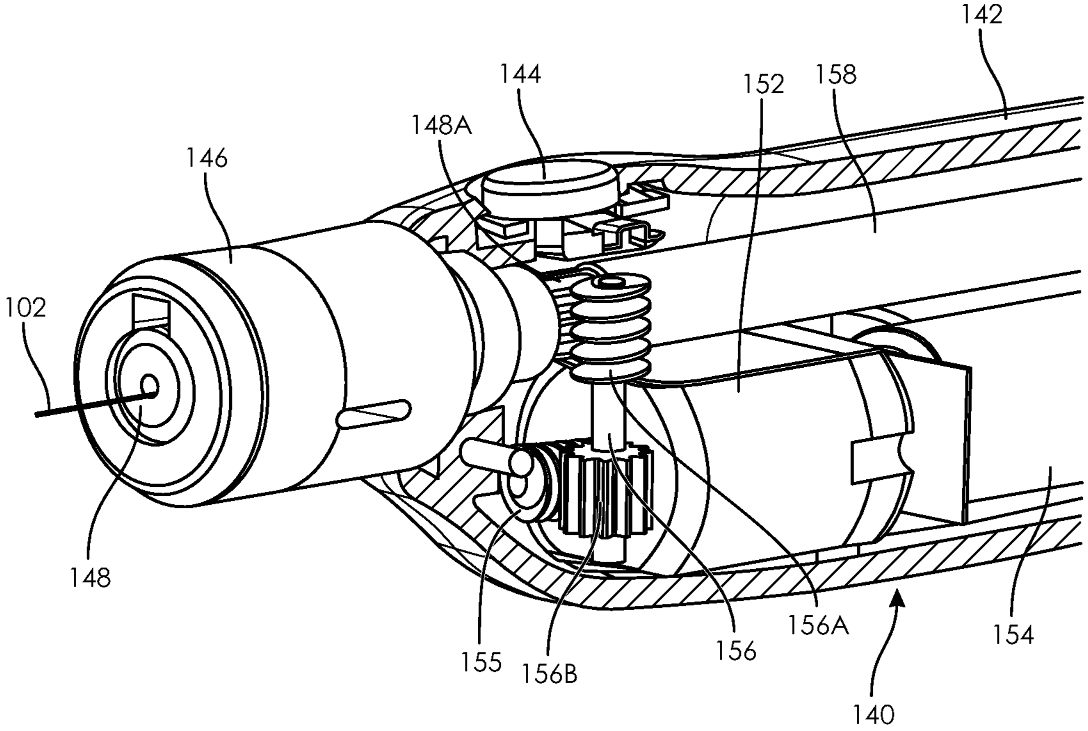
FIG. 14 illustrates a perspective open view of the guidewire manipulation device of FIG. 10.
Figure 15:
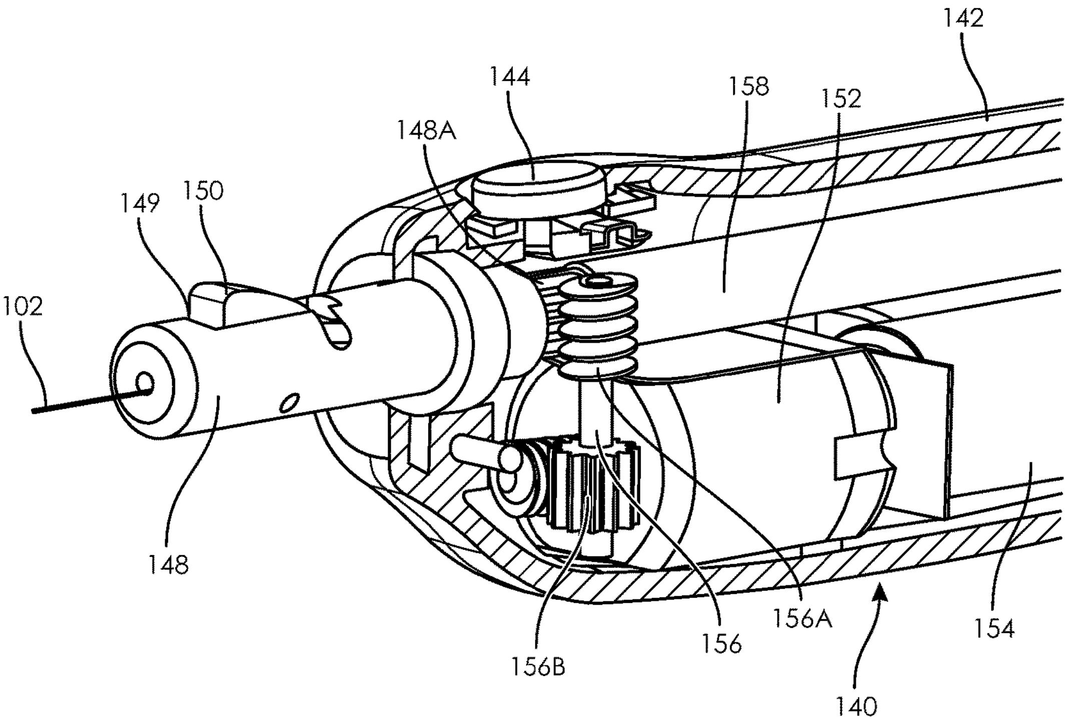
FIG. 15 illustrates a perspective open view of the guidewire manipulation device of FIG. 10.

FIGS. 10-15 illustrate another embodiment of a guidewire manipulation device 140 according to an embodiment of the present disclosure. The device 140 is generally similar to the previously described device 100. For example, the device 140 includes a hand-held (e.g., configured to be held within a user's hand), ergonomic, outer case 142 and a manipulation button 144. As best seen in FIGS. 11 and 12, the device 140 also includes a motor 152 powered by a battery 154 and a guidewire passage 158 configured for passing the guidewire 102.

Preferably, the device 140 includes a locking assembly in the form of a locking hub 146 (similar to the device 132) which allows the user to selectively lock the guidewire 102 with the device 140. The locking hub 146 allows free movement of the guidewire 102 when positioned near the case 142 (FIG. 11) and locks the guidewire 102 when the hub is pulled away from the case 142 (FIG. 12). The hub 146 includes an interior cavity with a top surface angled downward towards the case 142. Within the interior cavity is a locking wedge 150 which is located within a window 149 of a tube 148 that exposes the guidewire 102. In the unlocked position of FIG. 11, the hub 146 restrains the wedge 150 but does not press down on the wedge 150, thereby allowing the guidewire 102 to slide underneath the wedge 150. In the locked position of FIG. 12, the angled interior surface of the hub 146 forces the wedge downward against the guidewire 102, preventing the guidewire from movement relative to the device 140. A perspective view of the wedge 150 can also be seen in FIG. 15.

As seen in FIGS. 11-15, the motor 152 includes a worm 155 that engages a first gear section 156B of shaft 156. A worm 156A of shaft 158 engages gearing 148A on the outer surface of tube 148. In this respect, when the motor 152 is activated, it ultimately rotates the roller assembly, or tube 148. Thus, the hub 146 must be in a slid-out, locked position to cause the guidewire 102 to rotate.

As with all motorized embodiments described in this specification, the device 140 may also include a microprocessor and memory for storing and executing different rotation sequences (i.e., rotation directions and rotation speeds).

Figure 16:
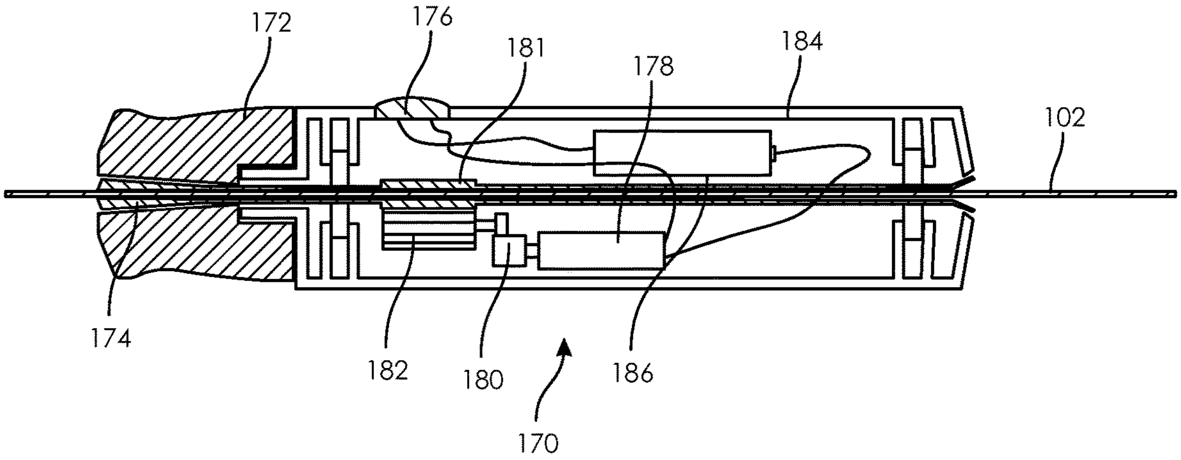
FIG. 16 illustrates a side open view of a guidewire manipulation device according to an embodiment of the present disclosure.
Figure 17:
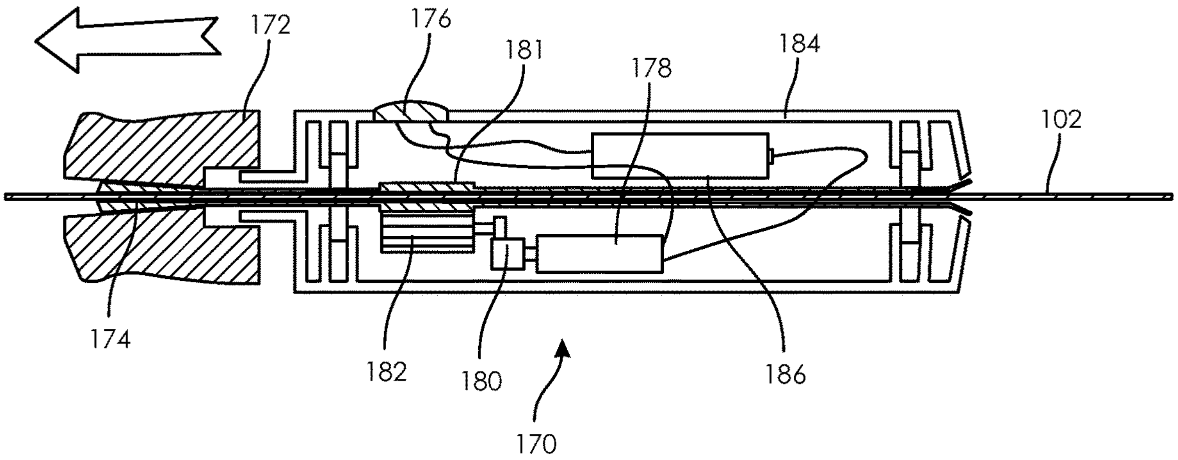
FIG. 17 illustrates a side open view of the guidewire manipulation device of FIG. 16.

FIGS. 16 and 17 illustrate a guidewire manipulation device 170 according to yet another embodiment according to the present disclosure. The device 170 is generally similar to previously described embodiments, including an outer case 184 having an actuation button 176 that is coupled to a battery 186 and a motor 178. The gear 180 of the motor 178 is engaged with a gear 182 that is also engaged with a geared section 181 on wedge tube 174.

A hub 172 includes an interior, angled passage that increases in diameter in a distal direction. The wedge tube 174 is partially positioned within the hub 172. In the unlocked position of FIG. 16, the angled passage of the hub 172 complements a distally expanding shape of the wedge tube 174, thereby preventing the wedge tube 172 from clamping or providing force on the guidewire 102 and thus allowing the guidewire 102 to slide and rotate relative to the device 170. In the looked position of FIG. 17, the hub 172 is moved distally from the case 184, causing the smaller diameter of the interior passage of the hub 172 to wedge or clamp on to the expanded distal end of the wedge tube 174. Thus, the wedge lobe 174 (preferably composed of a compressible, semi-compressible or deformable material) closes around the guidewire 102, maintaining the position of the guidewire 102 relative to the device 170 and further allowing rotation of the guidewire 102.

Figure 18:
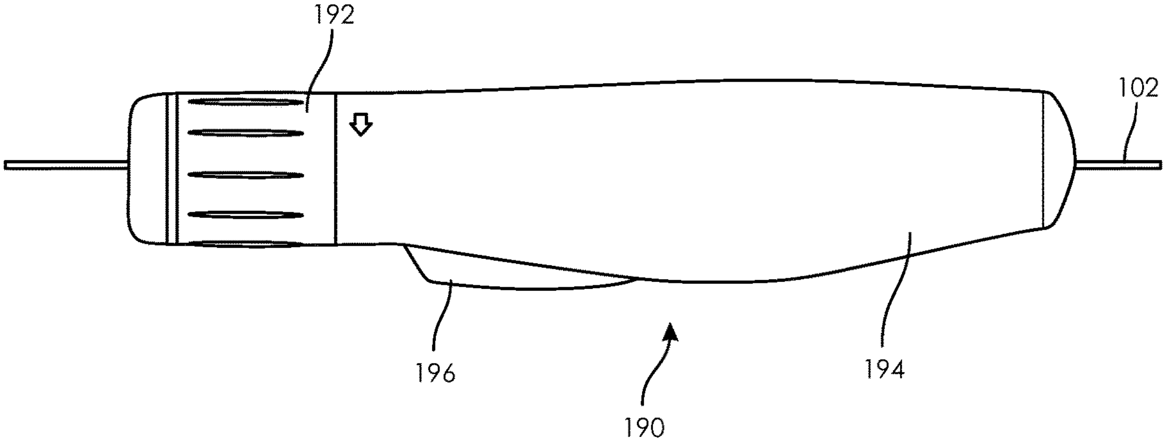
FIG. 18 illustrates a side view of a guidewire manipulation device according to an embodiment of the present disclosure.
Figure 19:
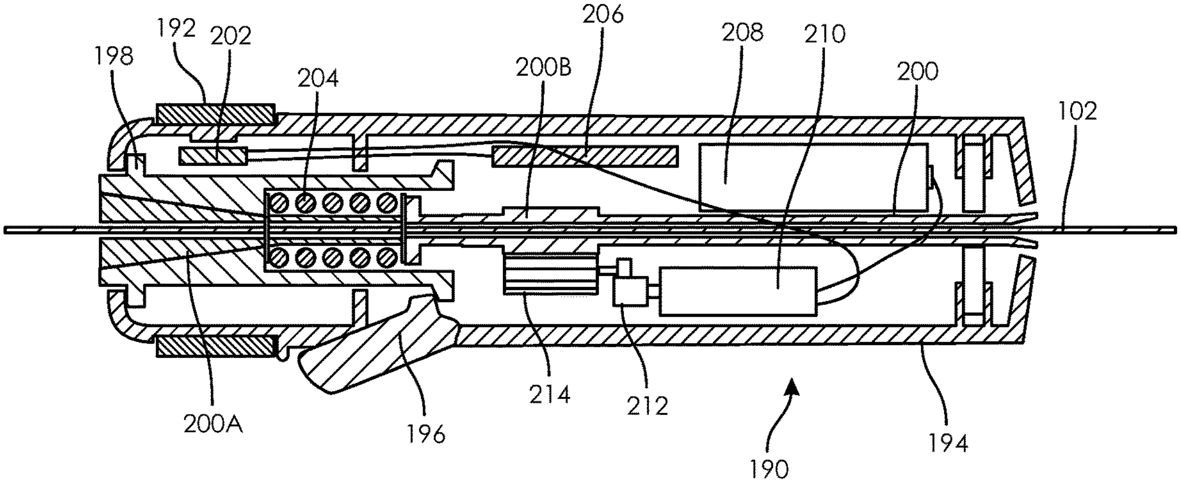
FIG. 19 illustrates a side open view of a guidewire manipulation device according to an embodiment of the present disclosure.
Figure 20:
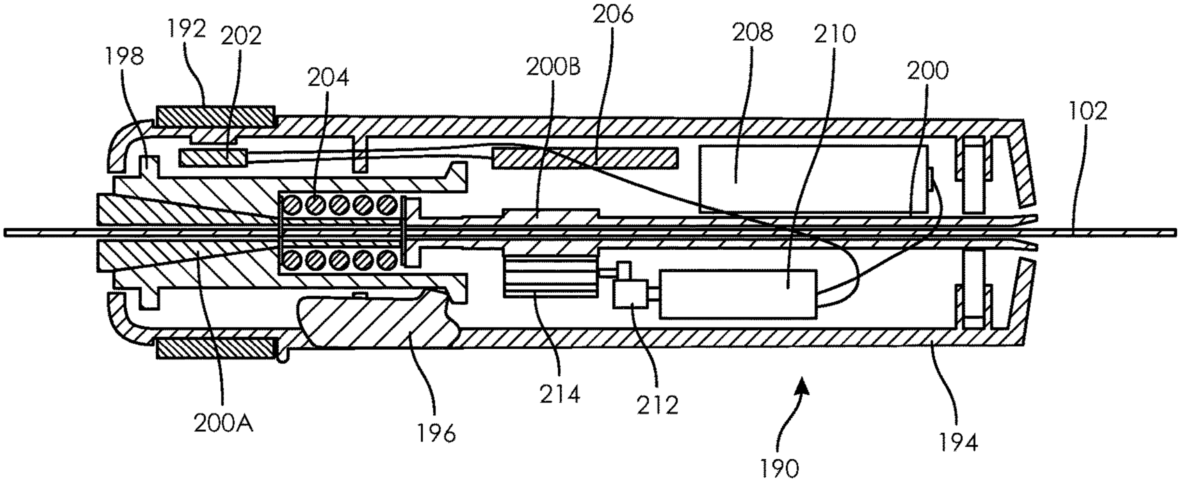
FIG. 20 illustrates a side open view of the guidewire manipulation device of FIG. 19.

FIGS. 18-20 illustrates another embodiment of a device 190 according to the present disclosure. The device 190 is generally similar to the previously described devices. However, the device 190 includes a locking assembly in the form of a guidewire lock activated by depressing a trigger 196. In this respect, the user can rotate hub 192, either clockwise or counter clockwise to respectively rotate the guidewire 102.

The device 190 is generally similar to the previously described embodiments, including a motor 210 powered by a battery 208, a gear 214 coupled to an output gear 212 of the motor 210 and to a geared portion 200B of a wedge tube

200 and a case 194 to contain the components. The motor 210 is controlled by a rocker switch 192 that is connected to a first circuit board 202 which sends the position of the rocker switch 192 to the second circuit board 206. The second circuit board 206 includes a microprocessor and memory for executing a plurality of rotation programs. These rotation programs direct the motor 210 to make predetermined rotation movements such as in a single direction, exponentially increasing rotational speed, quick rotation to cause vibration or a predetermined series of rotational movements. Thus, more complicated movements can be performed by the user.

The device 190 locks on to the guidewire 102 when the user releases trigger 196 (see FIG. 19) and unlocks the guidewire 102 when the user depresses trigger 196. The trigger 196 moves an outer tubing 198 which is biased in a distal direction by a spring 204. The interior passage of the outer tubing 198 increases in diameter in a distal direction forming an inverted cone shape. An inner wedge tube 200 is positioned within the passage of the outer tubing 198 and includes a wedge 200A that increases in size in a distal direction of the device 190. The guidewire 102 is located within a passage of the wedge tube 200.

When the trigger 196 is released, as in FIG. 19, the outer tubing 198 is moved distally by the spring 204, causing the smaller diameter region of the inner passage of the outer tubing 198 to press against the wedge 200A of wedge tube 200. The wedge 200 then compresses around the guidewire 102, locking the guidewire 102 in place relative to the device 190. When the trigger 196 is depressed, as in FIG. 20, a portion of the trigger 196 pushes the outer tubing 198 in a proximal direction, against the bias of the spring 204. The angled portions of the inner passage of the outer tubing 198 move away from the wedge 200*a*, allowing the inner passage of the wedge tube 200 to release the guidewire 102. Thus, the user can selectively lock on to and rotate the guidewire 102 (with the roller assembly, including wedge tube 200) by releasing the trigger 196 and pressing the actuation button 192.

Figure 21:
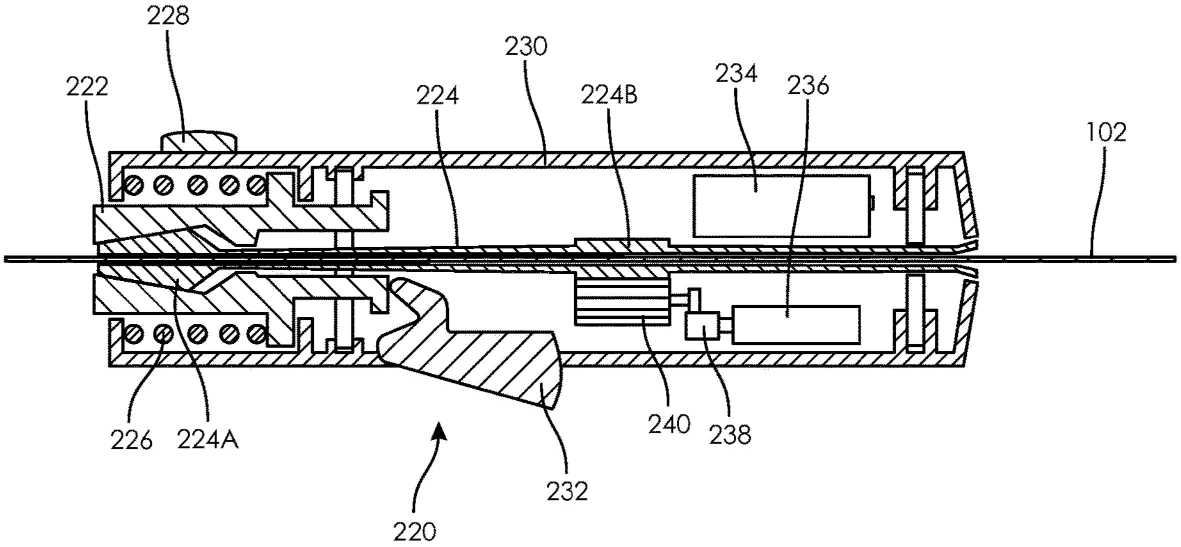
FIG. 21 illustrates a side open view of a guidewire manipulation device according to an embodiment of the present disclosure.
Figure 22:
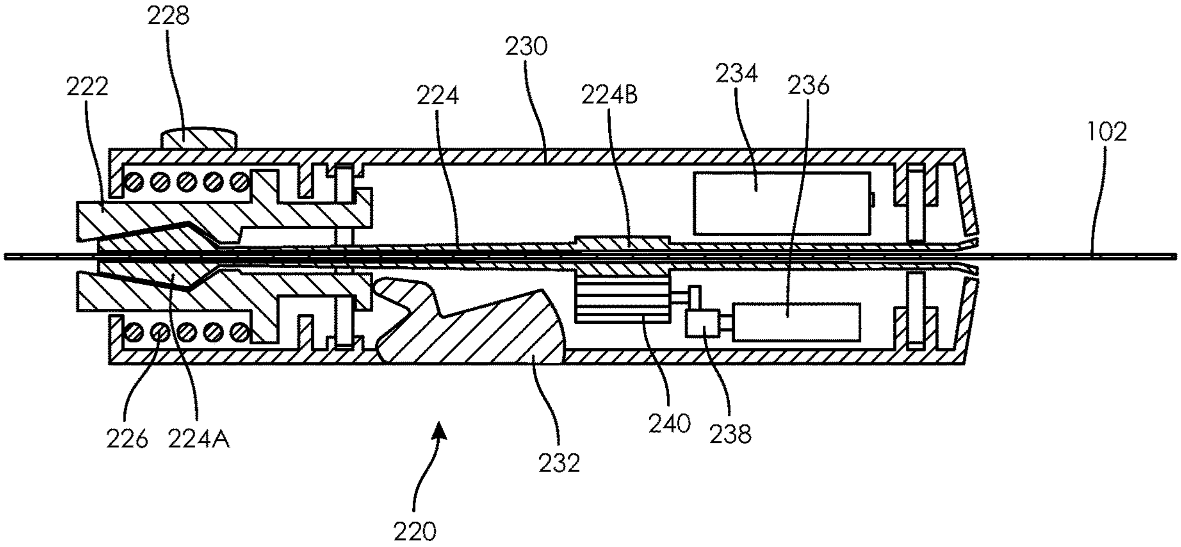
FIG. 22 illustrates a side open view of the guidewire manipulation device of FIG. 21.

FIGS. 21 and 22 illustrate another embodiment of a guidewire manipulation device 220 according to the present disclosure. The device 220 is generally similar to the previously described embodiments. Including a battery 234 powering a motor 236 which drives a wedge tube 224 (via a gear 240 connected to geared region 224B and output gear 238) and an actuation button 228.

The device 220 further includes a locking mechanism assembly that locks the lateral position of the guidewire 102. As seen in FIG. 21, when the user releases the trigger 232, the device remains in a locked position, allowing the user to rotate the guidewire 102. As seen in FIG. 22, when the user depresses the trigger 232, the device remains in an unlocked position, allowing the user to slide the device 220 along the guidewire 102 and preventing guidewire rotation.

In the locked position, the trigger 232 maintains an outer tube 222 in a proximal position, proximally biased by a spring 226. The outer tube includes an inner passage that generally decreases in diameter in a distal direction. The inner surface of the outer tube 222 presses against a wedge portion 224A of a wedge tube 224, causing the wedge tube 224 to press against and lock onto the guidewire 102.

In the unlocked position, the trigger 232 pushes the outer tube 222 distally, against the bias of the spring 226. The surface of the inner passage of the outer tube 222 moves away from the wedge 224A, releasing the wedge tube 224 from the guidewire 102.

The systems and methods disclosed herein further comprise a guidewire manipulation device for selectively imparting motive force (rotational and/or axial/longitudinal (linear) motion) to a guidewire. In use, such a guidewire manipulation device is selectively locked to a guidewire and is activated to impart motive force to maneuver the guidewire to a desired location during an endovascular procedure. The motive force applied to the guidewire is selectively rotational or axial to facilitate moving the guidewire through a vessel and/or penetrating occlusions.

Figure 23:
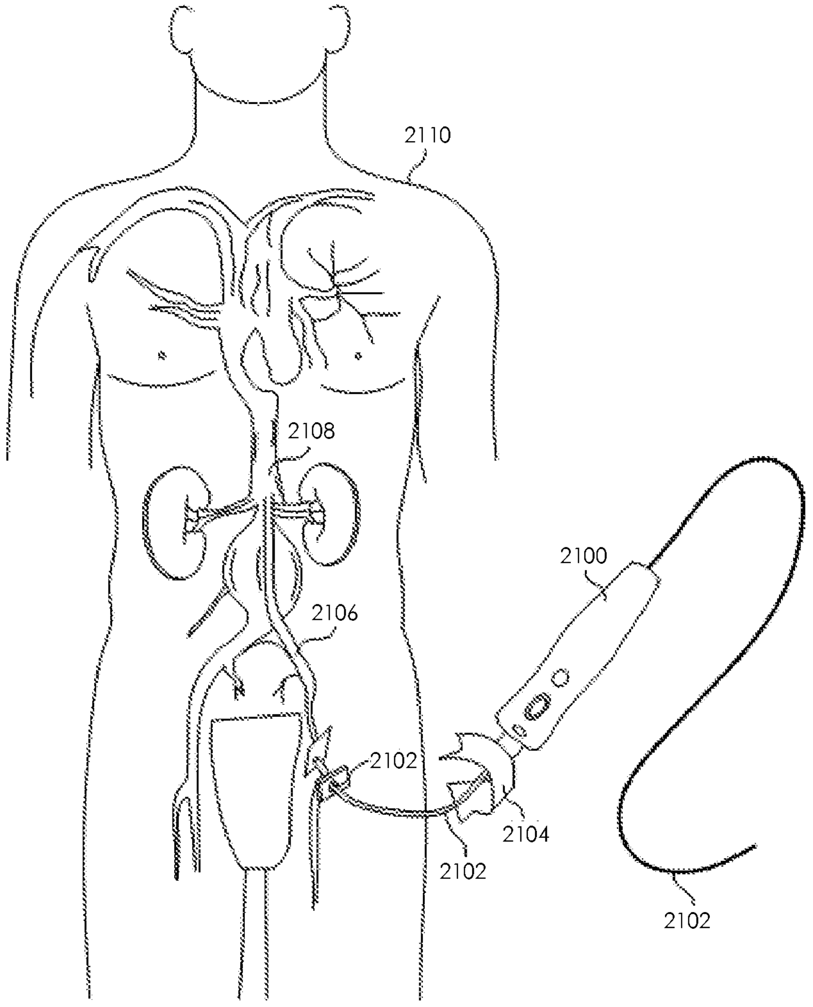
FIG. 23 illustrates a view of one embodiment of a guidewire manipulation device being used on a patient according to an embodiment of the present disclosure.

FIG. 23 illustrates a view of a guidewire manipulation device 2100 being used on a patient 2110 according to one embodiment of the present disclosure. In one embodiment, the guidewire manipulation device 2100 is a handheld device capable of fitting in the palm of a user's hand and being operated using one hand. In one embodiment, the guidewire manipulation device 2100 is advanced over a guidewire 2102, i.e., the guidewire 2102 passes through a longitudinally oriented passage in the device 2100. During an endovascular procedure, the guidewire 2102 is introduced into a vessel 2106 (e.g., a femoral artery) of the patient 2110. The guidewire manipulation device 2100 is selectively locked to the guidewire 2102. As the guidewire is advanced into the patient, the user operates the manipulation device 2100 to impart motive force (rotational and/or axial motion) to the guidewire 2102, as appropriate.

For example, as a distal end 2108 of the guidewire 2102 reaches an angled, curved, stenosed, or occluded region of the vessel 2106, the user locks the manipulation device 2100 to the guidewire and imparts rotational motive force to the guidewire 2102 (e.g., in a counter-clockwise direction indicated by arrow 2104), thereby causing the distal end 2108 of the guidewire 2102 to more easily advance through the angled, curved, stenosed, or occluded region of the vessel 2106. Once advanced past the region, the device 2100 is unlocked from the guidewire and the guidewire can be further advanced through the vessel. In another example, the distal end 2108 of the guidewire 2102 reaches an obstruction (e.g., an embolism, including, but not limited to a thromboembolism) but is unable to pass the obstruction. The user then locks the guidewire manipulation device 2100 to the guidewire 2102 and imparts a vibratory motion (e.g., rapidly oscillating between clockwise and counter-clockwise rotation). Such motion causes the distal end 2108 of the guidewire 2102 to pass through the obstruction. In another example, when the distal end 2108 of the guidewire 2102 reaches an obstruction, the user locks the guidewire manipulation device 2100 to the guidewire 2102 and imparts an axial motion (e.g., a linear movement of the guidewire 2102) to create a jackhammer effect. In another embodiment, the user may lock the device 2100 to the guidewire 2102 and simultaneously impart both rotational and axial motion to the guidewire 2102. In another embodiment of the present disclosure, a sequence of predefined guidewire manipulations (i.e., a pattern) may be produced using a computer program for controlling the motion as described in detail below. Various motive patterns to be selectively used in various surgical situations can be selected from memory and applied to the guidewire.

Figure 24:
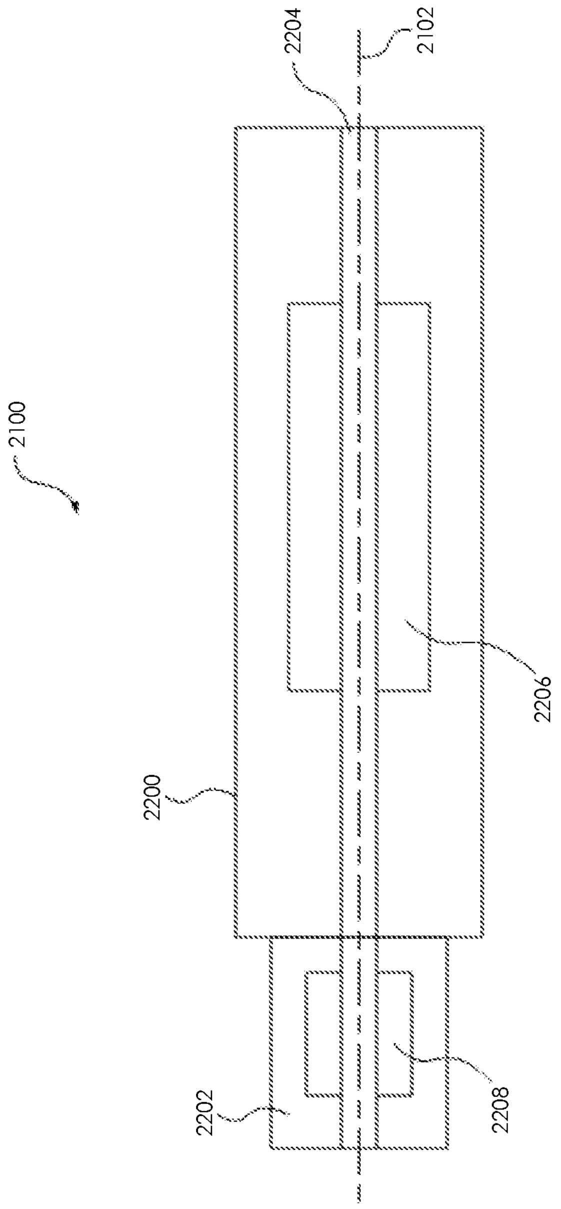
FIG. 24 depicts a schematic block diagram of a guidewire manipulation device according to an embodiment of the present disclosure.

FIG. 24 depicts a schematic block diagram of one embodiment of a guidewire manipulation device 2100. The guidewire manipulation device 2100 defines an axially longitudinal passage 2204 through which the guidewire 2102 is threaded during use. The guidewire manipulation device 2100 comprises a housing 2200, an actuator 2206, and a chuck 2202. The chuck 2202 comprises a guidewire locking mechanism 2208. During use, the chuck 2202 is locked to the guidewire 2102 using the looking mechanism 2208. Once locked, the actuator selectively imparts motive force (rotational motion and/or axial motion) to the guidewire 2102.

Figure 25:
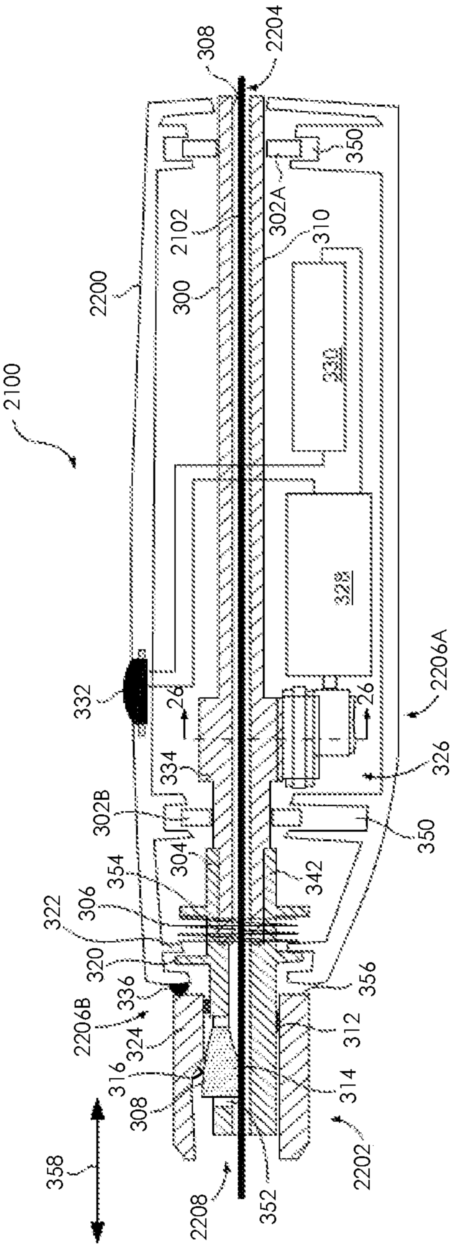
FIG. 25 depicts a vertical cross-sectional view of a guidewire manipulation device according to an embodiment of the present disclosure.

FIG. 25 depicts a vertical cross-sectional view of one embodiment of a guidewire manipulation device 2100. In this embodiment, the actuator 2206 of FIG. 24 is divided into a rotary actuator 2206A and an axial actuator 2206B such that the device may selectively apply to the guidewire: no motive force, rotary motive force or rotary and axial motive force.

Device 2100 comprises a housing 2200 typically formed into halves that are glued, bonded, screwed, or otherwise affixed to each other to form an enclosure. Within the housing 2200 are defined slots 350 wherein are retained bushings 302A and 302B. The bushings 302A and 302B support an axle 300 on its outer surface 310. The axle 300 defines the passage 2204 extending axially through the axle 300. When in use, the guidewire 2102 is threaded through the passage 2204.

The rotary actuator 2206A comprises the axle 300, a motor 328, a drive assembly 326, a controller 330, and a control switch 332. The drive assembly 326 couples rotational motion of the motor 328 to the axle 300 using a plurality of gears, further described with respect to FIG. 26 below. In one embodiment of the present disclosure, the controller 330 is simply one or more batteries that are coupled to the motor 328 via the control switch 332. In such an embodiment, the control switch 332 may simply apply a voltage from the one or more batteries to the motor 328 to cause the motor 328 to rotate. In its simplest form, the control switch 332 is a simple single-pole, single-throw (SPST), momentary contact switch. In other embodiments, the controller 330 comprises a programmable microcontroller as described with respect to FIG. 28 below. In other embodiments, the switch 332 may apply voltage to cause the motor 328 to selectively rotate clockwise or counter-clockwise. The control switch 332 is generally mounted to be exposed to the exterior of the housing 2200 and facilitate manipulation by one hand of a user (e.g., a thumb activated push-button or slide switch.

The axle 300 is coupled to a chuck 2202. In one embodiment, the chuck 2202 comprises a coupler 304, a hub 324 and a wedge 314. The coupler 304 and the axle 300 have splined mating surfaces 342 for coupling the rotational motion of the axle 300 to the chuck 2202, while allowing the coupler 304 to move in an axial direction. The hub 324 is threaded onto the coupler 304 at surface 312. The wedge 314 is located in a window 352 defined by the coupler 304. The hub 324 retains the wedge 314 within the window 352. In a disengaged (unlocked) position, the hub 324 does not impart pressure to the wedge 314 thereby allowing the guidewire 2102 to slide freely beneath the wedge 314 and through the passage 2204. To lock (engage) the guidewire into the lock mechanism 2208, the hub 324 is rotated relative to the coupler 304 such that the angled surface 316 of the hub 324 interacts with the top surface 308 of the wedge 314. As the hub 324 is moved relative to the coupler 304 via the mating threaded surfaces 312, the wedge 314 is forced against the guidewire 2102. Consequently, the guidewire 2102 is captured between the wedge 314 and the coupler 304 and thereby locked into the chuck 2202. Once locked, any motion of the chuck 2202 (e.g., rotational and/or longitudinal) is imparted as motive force to the guidewire 2102.

Other embodiments of the present disclosure utilize other forms of chucks. In a broad sense, any mechanism that can be used to selectively lock the guidewire to a source of motive force may be used. Other forms of chucks having multiple jaws or compressive slotted cylinders are applicable.

The coupler 304 comprises a spring seat 354 supporting a first end of a spring 306. The second end of spring 306 rests against a flange 322 that extends from the inner surface of the housing 2200. The spring 306 is one embodiment of a resilient member that biases the coupler 304 inwardly toward the axle 300. The coupler 304 further comprises a flange 320 that extends radially from the outer surface of the coupler 304. The flange 320 is positioned along the coupler 304 to limit the amount of axial movement that can be imparted to the chuck 2202. The flange 320 abuts the housing flange 322. As such, the spring 306 biases the coupler 304 to maintain contact between the flange 320 and the flange 322.

To impart axial (longitudinal) motion to the chuck 2202, the bottom surface 356 of the hub 324 is dimpled. The surface 356 interacts with a protrusion 336 extending from the exterior surface of the housing 2200 proximate the surface 356 of the hub 324. Depending on the position of the hub 324 relative to the coupler 304, the spring 306 insures that the protrusion 336 interacts with the dimpled surface 356. Upon locking the chuck 2202 to the guidewire 2102 and imparting rotation to the chuck 2202, the guidewire 2102 moves in an axial direction as indicated by arrow 358. To disengage the axial motive force, the hub 324 is rotated relative to the coupler 304 along the threads 312 to decouple the protrusion 336 from the surface 356. In this manner, the locking mechanism 2208 retains the guidewire 2102 such that rotational motion of the axle 300 is imparted to the guidewire 2102 without imparting axial motion. In this embodiment, the axial motion actuator 2206B comprises the hub 324, spring 306, coupler 304 and the housing 2200.

Figure 26:
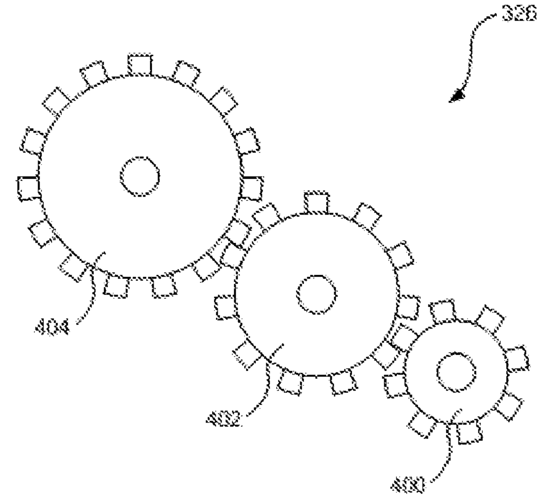
FIG. 26 depicts a portion of an actuator used in the guidewire manipulation device of FIG. 25.

FIG. 26 depicts a cross sectional view of the drive assembly 326 of the rotary actuator 2206A taken along line 26-26 of FIG. 25 in accordance with one embodiment of the present disclosure. The drive assembly 326 comprises a motor gear 400, an intermediary gear 402 and an axle gear 404. The motor 328 of FIG. 25 is coupled to the motor gear 400 to impart rotational motion to the motor gear 400. In one embodiment, the axle gear 404 is formed as an integral part of this surface of the axle 300 of FIG. 25. The intermediary gear 402 is designed to provide a gear ratio between the motor gear 400 and axle gear 404. The diameters and the number of teeth of each gear is considered to be a design choice that will define the speed of rotational motion of the guidewire 2102 as well as the oscillatory speed of the axial motion.

In other embodiments, the motor 328 of FIG. 25 may be coupled to the axle via other forms of drive assemblies, e.g., direct drive, worm gear, and/or the like. The specific motor and drive assembly characteristics are considered a design choice to develop specific guidewire rotation speed and torque. In some embodiments, the drive assembly may be adjustable to facilitate creating specific speed and torque profiles or adjustments. One form of adjustments may be facilitated by the use of a stepper motor that can be controlled with a pulse width modulated signal produced by the controller, as discussed below.

An alternative embodiment for imparting rotary motive force in selectable directions uses a gear train comprising two larger diameter spur gears mounted on a common shaft that is driven constantly in one direction by an electric motor. Each of the two spur gears has a section of its teeth, something over ½ its total number, removed. The removed sections of teeth are positioned such that only one or the other of two additional smaller spur gears, each located to be driven by one of these common shaft gears, will be driven at a time. The two smaller spur gears are then used one at a time to drive the gear on the axle, but the positioning of one additional gear between just one of these driving gears and the axle gear results in the rotational direction of the axle being reversed when that set is driving the axle gear.

Another embodiment, if only forward and reverse is required without a near constant rotational speed in either direction, has the spur gear on the axle driven by a pivoted ¼ pie-shaped plate. The toothed curved section opposite the pivot near the tip would be configured to have the correct pitch radius to mesh with the axle spur gear. This pivoted gear section plate would have, running upwards from its pivot, a slot in its face in which a pin, mounted off-center and a disc, could slide up and down freely. As an electric motor turns this disc in a constant direction, it would cause the pivoted plate to wobble back and forth so that its gear section drives the axle spur gear in one direction and then in the reverse direction.

Figure 27:
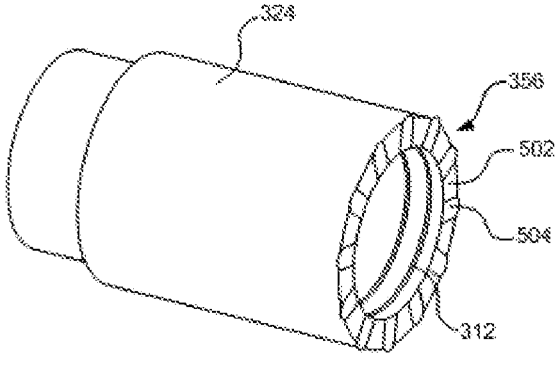
FIG. 27 depicts a perspective view of a hub of a chuck that imparts axial motive force to a guidewire when using the guidewire manipulation divisive FIG. 25.

FIG. 27 depicts a perspective view of the hub 324 in accordance with one embodiment of the present disclosure. The hub 324 comprises a surface 356 having a plurality of dimples 504 and spaces 502 between the dimples 504. The hub 324 further comprises a threaded interior surface 312. The threaded interior surface 312 is adapted to interact with a threaded exterior surface of the coupler 304 to adjust the position of the hub relative to the coupler 304 and the wedge 314. The dimples 504 and the spaces 502 between the dimples 504 are adapted to interact with the protrusion 336 to impart axial motion to the chuck 2202. The spacing of the dimples and the speed of the motor control the oscillation rate of the axial motion. Furthermore, the depth of the dimples 504 relative to the spaces 502 on the surface 356 controls the travel distance of the axial motion.

Figure 28:
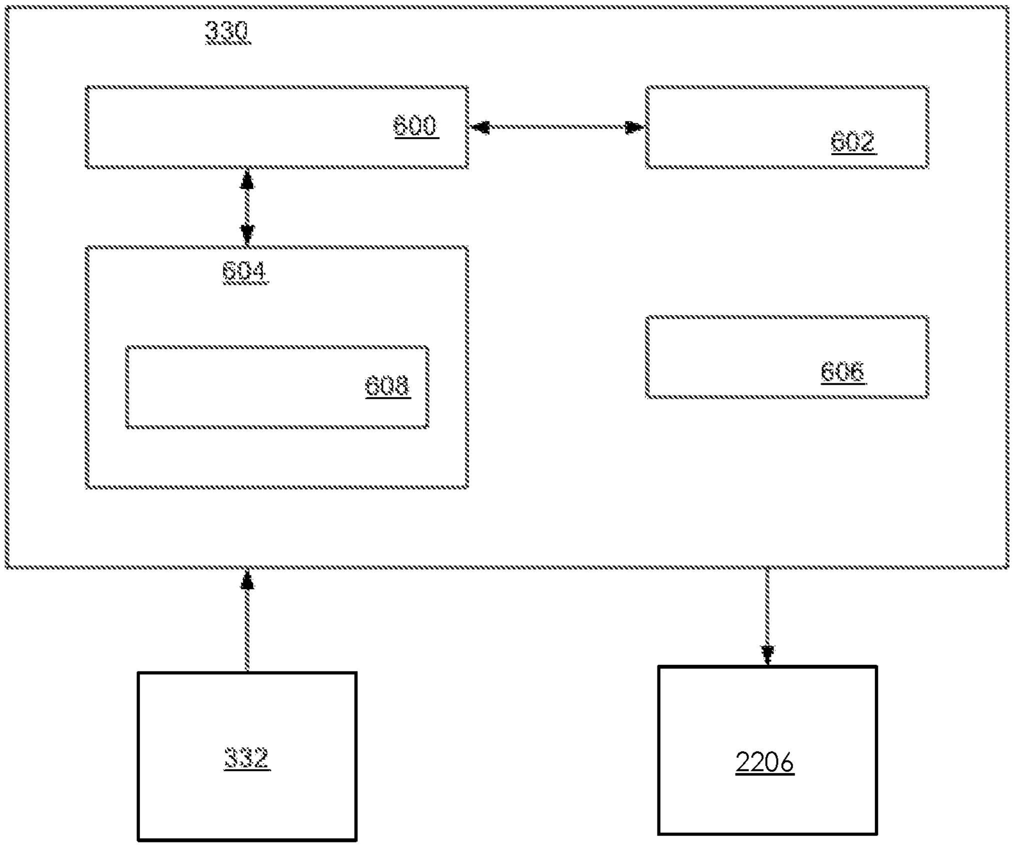
FIG. 28 depicts a block diagram of a controller for a guidewire manipulation device in accordance with an embodiment of the present disclosure.

FIG. 28 depicts a block diagram of the controller 330 in accordance with one embodiment of the present disclosure. The controller 330 comprises a microcontroller 600, support circuits 602, memory 604 and a power supply 606. The microcontroller 600 may be one or more of many commercially available microcontrollers, microprocessors, application specific integrated circuits (ASIC), and the like. The support circuits 602 comprise well known circuits that facilitate the operation of the microcontroller 600 including, but not limited to, clock circuits, cache, power supplies, input/output circuits, indicators, sensors, and/or the like. In one embodiment, the power supply 606 comprises one or more batteries. In other embodiments, the power supply 606 may comprise an AC to DC converter to allow the guidewire manipulation device to be plugged into a wall socket. In further embodiments, the power supply 606 may comprise one or more batteries and a charging circuit for the batteries may be inductively coupled to a base charger.

The memory 604 may be any form of memory device used to store digital instructions for the microcontroller 600 as well as data. In one embodiment, the memory 604 is random access memory or read only memory comprising control code 608 (e.g., computer readable instructions) that are used to control the actuator 2206 to impart motion to the guidewire 2102. The programs utilized by the microcontroller 600 to control the actuator 2206 are generally controlled by the control switch 332 and/or another input device.

In one embodiment of the present disclosure, the motor 328 is a stepper motor that is controlled using, for example, a pulse width modulated signal produced by the controller 330 to impart specific torque and/or speed profiles to the motor 328. In some embodiments, predefined programs can be generated and selected through manipulation of the switch 332 to enable a user to overcome specific types of obstructions within the path of the guidewire. For example, if a surgeon encounters a specific type of embolism, a specific program defining the motion of the guidewire to overcome the obstruction can be selected and implemented. Various programs can be generated through empirical study of guidewire utilization in endovascular procedures. To select a particular motion pattern, the switch may be a slide switch having a plurality of selectable positions, where each position corresponds to a different motion pattern.

Figure 29:
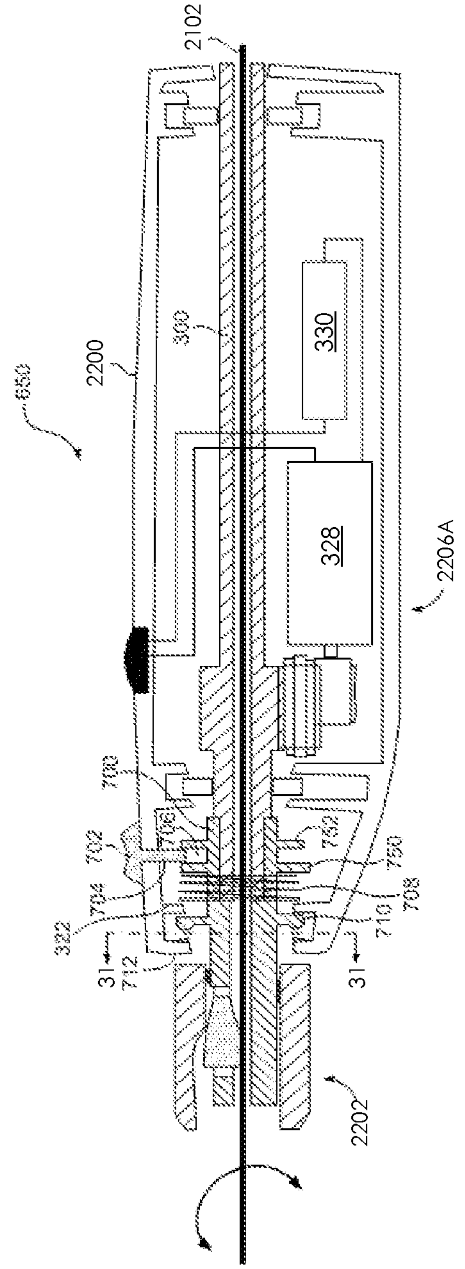
FIG. 29 depicts a vertical cross-sectional view of alternative embodiment of the guidewire manipulation device.

FIG. 29 depicts a vertical cross-sectional view of a guidewire manipulation device 650 according to an alternative embodiment of the present disclosure. In this embodiment, the use of axial motion is selected through manipulation of a mechanical switch 702. As with the prior embodiment, this embodiment selectively imparts to a guidewire: no motive force, rotary motive force, or rotary and axial motive force. The device 650 comprises a rotational actuator 2206A as described above with respect to FIG. 25. In this embodiment, a coupler 700 comprises a spring seat 750, a dimpled flange 710 and a switch stop 752. A slidable switch 702 comprises an extension 704 that interacts with a switch seat 752. The switch seat 752 and the spring seat 750 define a space 706 that captures the switch extension 704. Manipulation of the switch 702 causes the coupler 700 to move axially along the surface that mates with the axle 300. A spring 708 is positioned between the spring seat 750 and the housing flange 322. The spring 708 biases the coupler 700 inwardly toward the axle 300. The dimpled flange 710 radially extends from the coupler 700. One surface of the dimpled flange 710 abuts the housing flange 322 to limit the distance the coupler 700 moves in an axial direction. The dimpled flange 710 has a surface aligned with a dimpled surface 712 of the housing 2200. When the guidewire 2102 is locked to the chuck 2202 and the rotational actuator 2206A is activated, the guidewire 2102 rotates without any axial movement. As described further with respect to FIG. 32 below, when the switch 702 is moved forward to cause the dimpled surface of flange 710 to engage the dimpled surface 712, the guidewire 2102 axial motive force is imparted to the guidewire 2102.

Figure 30:
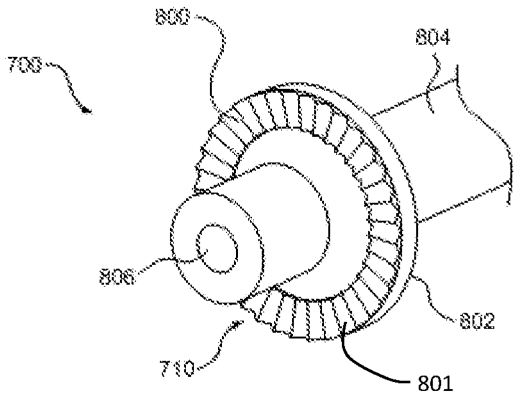
FIG. 30 depicts a partial perspective view of a portion of a guidewire drive assembly for the guidewire manipulation device of FIG. 29.

FIG. 30 depicts a partial perspective view of the coupler 700 in accordance with one embodiment of the present disclosure. The coupler 700 has an aperture 806 through which the guidewire 2102 is threaded. The dimpled flange 710 comprises a radially extending flange 802 having a plurality of dimples 800 formed in the surface 801. In one embodiment, the dimples 800 are formed as a sequence of wedges. In other embodiments, to cause axial motion of the chuck when the coupler 700 is rotated, the surface 801 of the flange 802 is varied such that interaction with a corresponding surface causes axial movement of the coupler 700.

Figure 31:
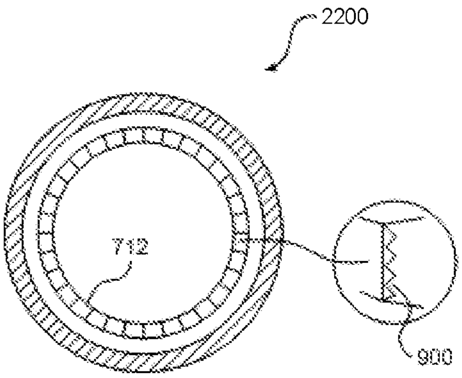
FIG. 31 depicts a cross-sectional view of a portion of the housing for the guidewire manipulation device of FIG. 29.

FIG. 31 depicts a cross-sectional view of the housing 2200 taken along line 31-31 in FIG. 29. In one embodiment, the surface 712 comprises corresponding protrusions shaped to interact with the dimples 800 in the surface 801 of the coupler 700. In another embodiment, the surface 712 may comprise complementary wedges 900 to the surface 801 of the coupler 700. The shape of the wedges 900 defines, in part, the distance travelled, the rate of acceleration of the guidewire 2102, and the speed of the oscillation of the guidewire 2102.

Figure 32:
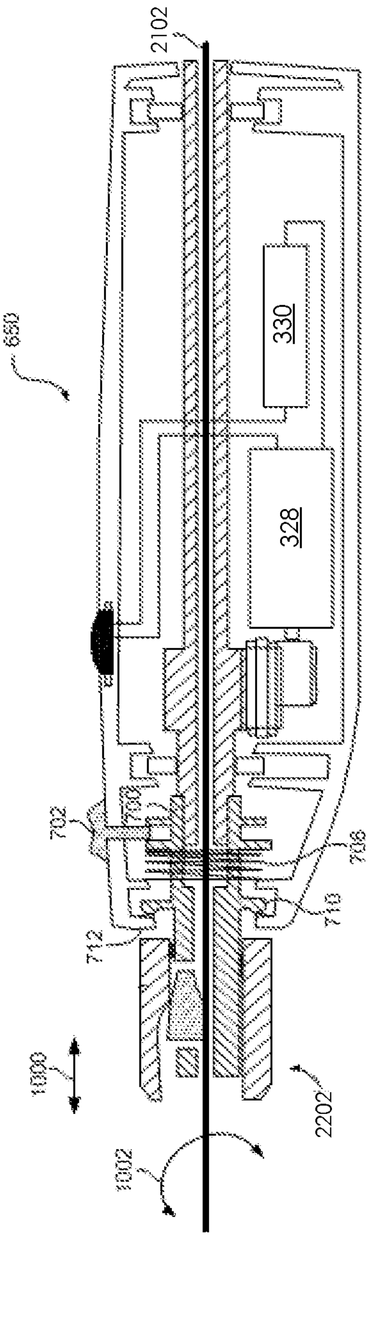
FIG. 32 depicts a vertical cross-sectional view of the guidewire manipulation device of FIG. 29 having the actuator engaged to apply axial motive force to the guidewire in accordance with one embodiment of the present disclosure.

FIG. 32 depicts an embodiment of the guidewire manipulation device 650 of FIG. 29 where the dimpled flange 710 has been engaged the protrusion surface 712. In this manner, the switch 702 has moved the coupler 700 forward to facilitate engagement of the surfaces 710 and 712. When the chuck 2202 locks to the guidewire 2102 and the rotary actuator is activated, the guidewire 2102 rotates as shown in arrow 1002 and axially oscillates as represented by arrow 1000.

Figure 33:
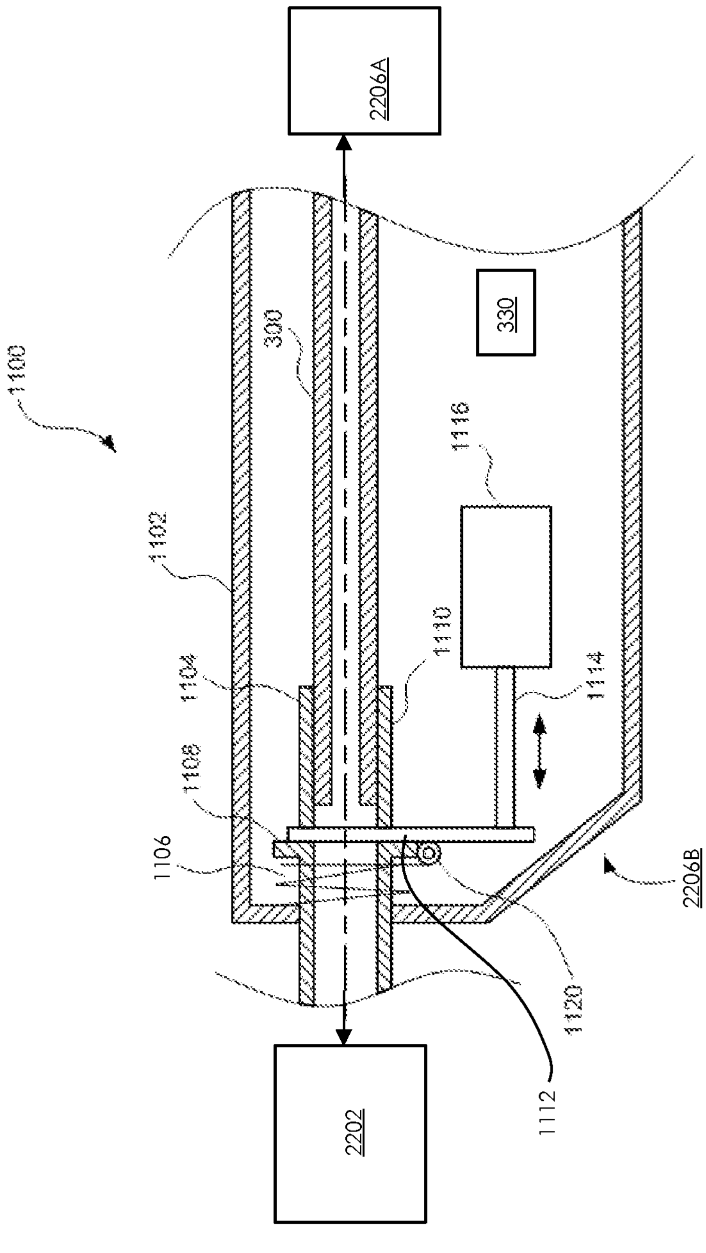
FIG. 33 depicts a partial, vertical cross-sectional view of another embodiment of a guidewire manipulation device for imparting axial motive force to a guidewire.

FIG. 33 depicts a vertical cross-sectional view of a portion of a guidewire manipulation device 1100. Device 1100 comprises an axial actuator 2206B that can be selectively utilized without imparting rotational motion of the guidewire. As such, with this embodiment, the device 1100 selectively imparts to the guide wire: no motive force, rotary motive force, axial motive force, or axial and rotary motive force.

In one embodiment, the device 1100 comprises a linear actuator 1116 coupled to a shaft 1114 that interacts with a fulcrum 1112. The linear actuator 1116 imparts linear motion to one portion of the fulcrum 1112. The fulcrum is mounted upon a pivot point 1120 such that the fulcrum 1112 rotates about the pivot point 1120 as a linear motive force is applied to the fulcrum 1112. A second end of the fulcrum 1112 interacts with a coupler 1104. The coupler 1104, as with prior embodiments, has a splined surface that interacts with the axle 300 to impart rotational motion to the coupler 1104, as needed. The coupler 1104 comprises a spring seat 1108. A spring 1106 is positioned between the housing 1102 and the spring seat 1108 to bias the coupler 1104 toward the axle 300. The fulcrum 1112 couples to the spring seat 1108 such that motion of the fulcrum 1112 axially moves the coupler 1104. In this manner, without any rotational motion the linear actuator 1116 imparts axial motion to the coupler 1104 and to guidewire 2102 locked in the chuck 2202.

In one embodiment, the linear actuator 1116 may be a solenoid, piezoelectric actuator, linear motor, rotary motor and ball screw or rack/pinion, and/or the like. In another embodiment, a hammer-drill type assembly may be used to impart axial force to the guidewire.

The controller 330 in a manner similar to that described for controlling the motor 328 of FIG. 25 may control the linear actuator 1116.

Figure 34:
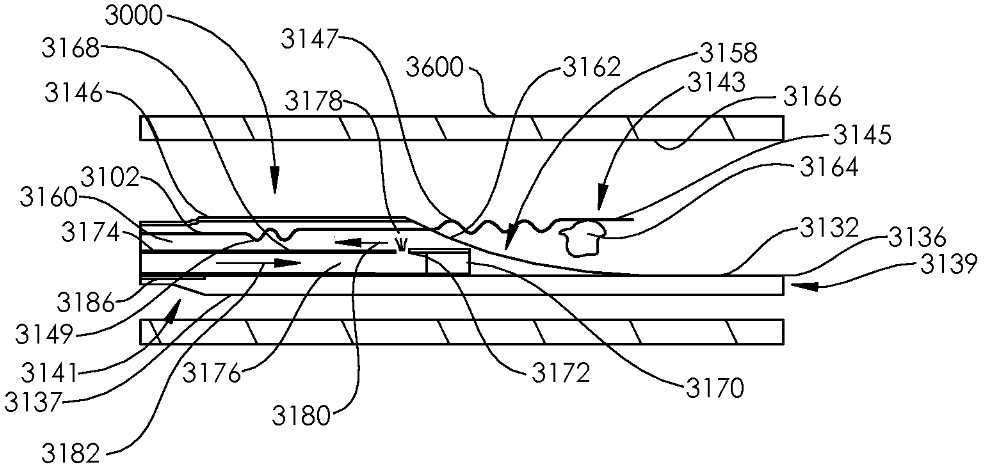
FIG. 34 illustrates an aspiration catheter within a blood vessel being used in conjunction with a guidewire which is moved by a guidewire manipulation device, according to an embodiment of the present disclosure.

FIG. 34 shows an open distal end 3158 of an aspiration lumen 3160 of an aspiration catheter 3000 for aspirating thrombus within a blood vessel 3600. A skive 3162 may be formed in a polymer jacket 3146 of the aspiration catheter 3000, to aid entry of a thrombus 3164 that is aspirated into the aspiration lumen 3160 (in the direction of arrow 3180) by the combination of the vacuum created by a vacuum source (e.g., VacLok® Syringe, vacuum bottle) and the injection of fluid into the distal end of the aspiration lumen 3160, as described below. The skive 3162 also minimizes the chances of the open distal end 3158 being sucked against a blood vessel wall 3166. A distal supply tube 3168 of the aspiration catheter 3000 has a closed distal end 3170. For example, it may be occluded during manufacture using adhesive, epoxy, hot melt adhesive or an interference member, such as a metallic or polymeric plug. However, in some embodiments, the aspiration catheter 3000 may have a blunt or non-angled tip, instead of the skive 3162. Alternatively, the distal supply tube 3168 may be closed off by melting a portion of it. The distal supply tube 3168 has a lumen 3176 extending its length and an orifice 3172 formed through its wall 3174 at a location adjacent and proximal to the closed distal end 3170. The orifice 3172 may have a diameter between about 0.0508 mm (0.002 inches) and about 0.1016 mm (0.004 inches), or about 0.0787 mm (0.0031 inches). The inner diameter of the distal supply tube 3168 may be between about 0.3048 mm (0.012 inches) and about 0.4826 mm (0.019 inches), or between about 0.3556 mm (0.014 inches and about 0.4318 mm (0.017 inches) or about 0.3937 mm (0.0155 inches). The lumen 3176 of the distal supply tube 3168 is a continuation of an overall flow path emanating from a fluid source (e.g., saline bag, saline bottle) including an extension tubing (not shown). In some embodiments, the lumen 3176 of the distal supply tube 3168 may taper, for example, from an inner diameter of about 0.3937 mm (0.0155 inches) at a proximal portion to an inner diameter of about 0.2974 mm (0.011 inches) at a distal portion. In some embodiments, the equivalent of a taper may be achieved by bonding different diameter tubing to each other, resulting in a stepped-down tubing inner diameter. In some embodiments, different diameter tapered tubing may be bonded to each other, for a combination of tapering and step-down of diameter. An output pressure wave (for example, of saline injected via a pump) causes a liquid injectate to flow through the flow path, including a distal supply tube 3168 (arrow 3182), and causes a fluid jet 3178 to exit the orifice 3172 at a high velocity. The fluid jet 3178 serves to macerate thrombus 3164 that is sucked into the aspiration lumen 3160, and also can serve to dilute the thrombus. This maceration and dilution assures that there is continuous flow through the aspiration lumen 3160 so that it will not clog. The fluid jet 3178 is configured to be contained within the aspiration lumen 3160, and to not exit into a blood vessel or other body lumen. A guidewire tube 3132 having a distal end 3136 and a proximal end 3137 and having a distal port 3139 and a proximal port 3141 is secured to the aspiration catheter 3000 with attachment materials 3186. Though the guidewire tube 3132 of FIG. 34 is shown having a length that is shorter than the length of the aspiration catheter 3000 (sometimes referred to as a rapid exchange catheter), in other embodiments, the guidewire tube 3132 may extend substantially the entire length of the aspiration catheter 3000. In some embodiments, the aspiration catheter 3000 may have a length of between 100 cm and 180 cm, and the guidewire tube 3132 may have a length of 28 cm or less. In some embodiments, the guidewire tube 3132 may be a length of 25 cm or less. In some embodiments, the guidewire tube may have a length of 10 cm or less. In some embodiments the guidewire tube may have a length of 3 cm or less. In some embodiments, the guidewire tube may have a length of between about 3 cm and about 28 cm. The guidewire tube 3132 may be located adjacent (i.e., lateral) to the aspiration lumen 3160, or may be located co-axially within the aspiration lumen 3160. An additional guidewire 3102 may be used along with any aspiration catheter (including, for example, the aspiration catheter 3000) to facilitate the movement of aspirated or macerated thrombus through a catheter lumen, for example, through the aspiration lumen 3160 of the aspiration catheter 3000. The guidewire 3102 is secured at its proximal end 3188 (FIG. 37) to any of the embodiments of the guidewire manipulation device 100, 132, 140, 170, 190, 220, 2100, 650, 1100. A distal end 3143 may include a straight portion 3145 or a curved portion 3147, or a combination of a straight portion 3145 and a curved portion 3147. The guidewire 3102 may include a curved portion 3149 which is not located at the very distal end 3143. The curved portion 3147, 3149 may comprise a single arc or multiple arcs, but may generally comprise any non-straight pattern. The one or more arcs may be contained within a plane, or they may be three-dimensional. The curved portion 3147, 3149 may comprise a helix, such as a single diameter helix or a tapering diameter helix. The tapering diameter helix may taper such that the diameter increases as it extends distally, or such that the diameter decreases as it extends distally. In some cases, a fully straight guidewire 3102 may be used.

In FIG. 34, either the straight portion 3145 of the distal end 3143 or the curved portion 3147 of the distal end 3143 (or both in combination) may be placed adjacent or within the thrombus 3164 by inserting the guidewire 3102 through the aspiration lumen 3160 of the aspiration catheter 3000, and then operating the guidewire manipulation device 100, 132, 140, 170, 190, 220, 2100, 650, 1100 to rotate, longitudinally cycle, or otherwise move the guidewire 3102. The movement caused at the distal end 3143 of the guidewire 3102 serves to help to break up or macerate the thrombus 3164, and also help to move the partially or completely macerated thrombus 3164 (or a portion thereof) towards the aspiration catheter 3000 and particularly towards the open distal end 3158 of the aspiration lumen 3160 of the aspiration catheter 3000. The curved portion 3149 within the aspiration lumen 3160 of the aspiration catheter 3000 also serves to facilitate the movement of the partially or completely macerated thrombus 3164 (or a portion thereof) through the aspiration lumen 3160 of the aspiration catheter 3000, towards a proximal end of the aspiration lumen 3160. The curved portion 3149 may also serve to help center the guidewire 3102 within the aspiration lumen 3160 or to stabilize the guidewire 3102 as it is rotated or longitudinally moved by the guidewire manipulation device 100, 132, 140, 170, 190, 220, 2100, 650, 1100. In some cases, the guidewire 3102 may be slowly pulled proximally during the aspiration of the thrombus 3164, so that the curved portion 3149 helps to translate portions of thrombus. In some embodiments, the curved portion 3149 may be replaced by a straight portion. For example, a guidewire may comprise an outer coil extending along its longitudinal axis, which comprise external contours that will serve to macerate or translate a portion of thrombus. The guidewire manipulation device 100, 132, 140, 170, 190, 220, 2100, 650, 1100 may be operated such that the guidewire 3102 is rotated in a direction such that the curved portion 3149 (or the straight portion of helical coil) rotates in a direction that preferentially moves the portion of thrombus proximally in the aspiration lumen, in a similar action to an impeller or Archimedes screw. If the aspiration lumen 3160 of the aspiration catheter 3000 becomes clogged with thrombus or other embolus, the guidewire manipulation device 100, 132, 140, 170, 190, 220, 2100, 650, 1100 may be attached to a guidewire 3102 that is already in place (i.e., through a guidewire lumen) to guide the catheter, and then the guidewire manipulation device may be activated to move (rotate, longitudinally translate, etc.) the guidewire 3102 to help dislodge the thrombus or other embolus so that it can be fully aspirated/evacuated and removed from the aspiration lumen 3160, thus eliminating the clog. The guidewire 3102 or other elongate medical devices may be fabricated from a number of different biocompatible materials, including, but not limited to stainless steels or shape-memory alloys such as nickel-titanium alloys (Nitinol).

Figure 35:
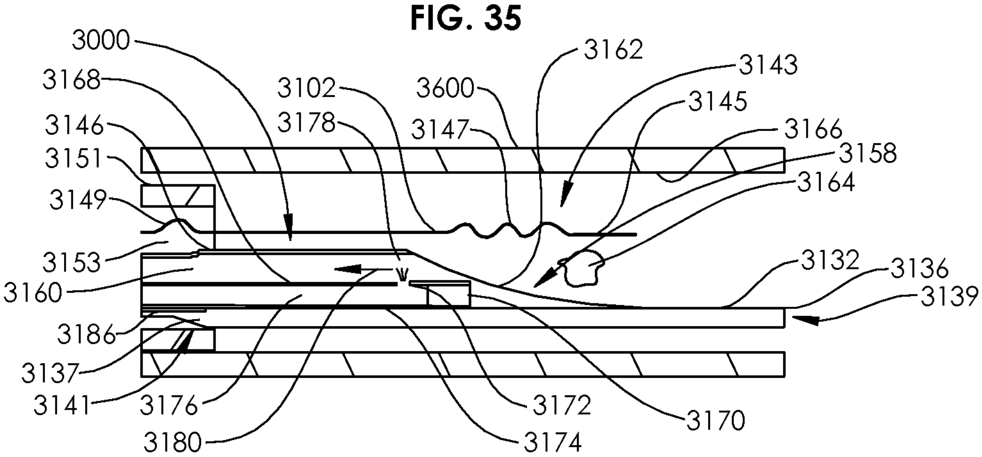
FIG. 35 illustrates an aspiration catheter within a blood vessel being used in conjunction with a guidewire which is moved by a guidewire manipulation device, according to another embodiment of the present disclosure.

In FIG. 34, both the aspiration catheter 3000 and the guidewire 3102 may be inserted (separately or together) through a delivery catheter, such as a coronary guiding catheter. FIG. 35 illustrates the aspiration catheter 3000 and a guidewire 3102 inserted through a delivery catheter 3151, such as a coronary guiding catheter, but in this case, the guidewire 3102 is radially adjacent the aspiration catheter, within an annulus between the interior of the delivery catheter 3151 and the exterior of the aspiration catheter 3000. Thus, the guidewire 3102 may be moved or manipulated by the guidewire manipulation device 100, 132, 140, 170, 190, 220, 2100, 650, 1100 such that the distal end 3143 aids the maceration or movement of the thrombus 3164 not only into the aspiration lumen 3160 of the aspiration catheter 3000, but also into the lumen 3153 of the delivery catheter 3151. The curved portion 3149 (or a straight portion) is configured to aid the movement of the thrombus 3164 (or a portion thereof) through the lumen 3153 of the delivery catheter 3151. In some cases, the guidewire 3102 may be slowly pulled proximally during the aspiration of the thrombus 3164, so that the curved portion 3149 helps to translate portions of thrombus 3164. In other embodiments, two guidewires 3102 and two guidewire manipulation devices 100, 132, 140, 170, 190, 220, 2100, 650, 1100 may be used, in a combination of the methods of FIG. 34 and FIG. 35. The aspiration catheters described herein may include any standard aspiration catheter having one or more aspiration lumens. Aspiration catheters used herein may include the ACE™ or INDIGO® catheters produced by Penumbra, Inc. of Alameda, Calif., USA.

Aspiration catheters and aspiration systems may include those described in U.S. Patent Application Publication No. 2015/0282821 to Look et al., published Oct. 8, 2015, which is incorporated herein by reference in its entirety for all purposes.

Aspiration catheters and aspiration systems may include those described in U.S. Patent Application Publication No. 2015/0327875 to Look et al., published Nov. 19, 2015, which is incorporated herein by reference in its entirety for all purposes.

Figure 38:
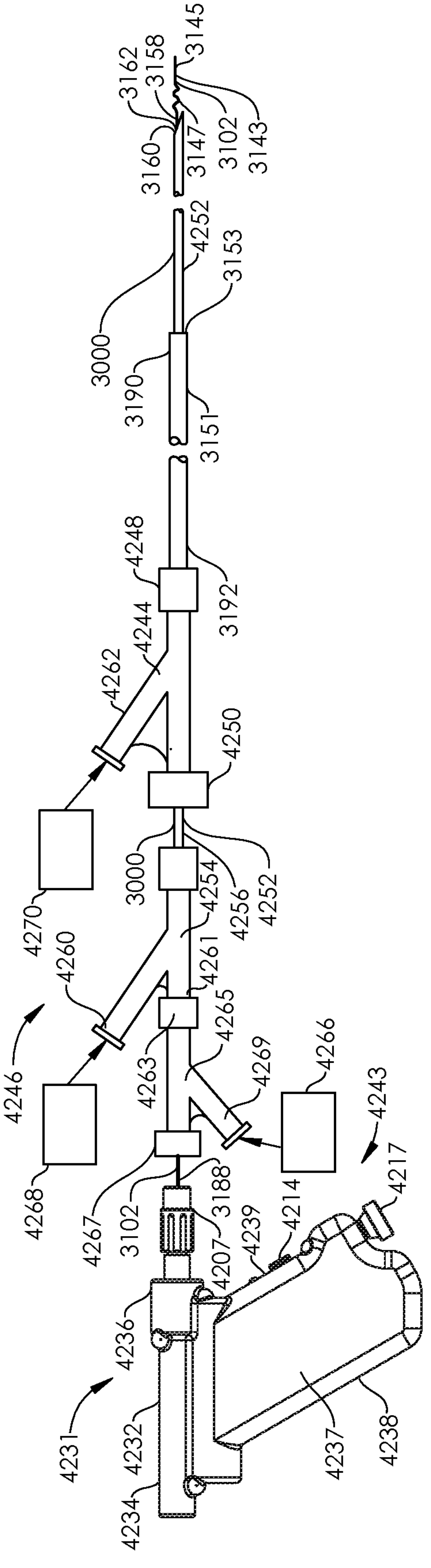
FIG. 38 illustrates a plan view of a system for treating a patient having thrombus, according to an embodiment of the present disclosure.

FIG. 38 illustrates a system for treating thrombus 4246. The system for treating thrombus 4246 includes a delivery catheter 3151 having a lumen 3153 through which an aspiration catheter 3000 is placed. A guidewire 3102 may be inserted either through the lumen 3153 of the delivery catheter 3151, or (as shown in FIG. 38) through a lumen of the aspiration catheter 3000, for example, through the aspiration lumen 3160 of the aspiration catheter 3000. The guidewire 3102 is configured to be manipulated (rotationally and/or longitudinally) by a guidewire manipulation device 4231 having a housing 4232 and a handle 4237. The guidewire manipulation device 4231 may include any of the embodiments described herein, or may include embodiments of guidewire manipulation devices such as those disclosed in co-pending U.S. patent application Ser. No. 15/235,920, filed on Aug. 12, 2016 and entitled "System and Method for Manipulating an Elongate Medical Device," which is incorporated by reference herein in its entirety for all purposes. The delivery catheter 3151 has a proximal end 3192 and a distal end 3190, with the proximal end 3192 coupled to a y-connector 4244 by a luer connection 4248. The luer connection 4248 may include in some embodiments a female luer attached to the proximal end 3192 of the delivery catheter 3151 and a male luer at the distal end of the y-connector 4244. A hemostasis valve 4250 at the proximal end of the y-connector 4244 is configured to seal around a shaft 4252 of the aspiration catheter 3000, and may include a Touhy-Borst, a spring-loaded seal, a duckbill seal, or other seals. A connector 4254 is attached to the proximal end 4256 of the aspiration catheter 3000. The connector 4254 includes a central bore 4258 which is in fluid communication with the aspiration lumen 3160, and which terminates in a connector 4261 (for example, a female luer connector). In embodiments wherein the aspiration catheter 3000 comprises a forced aspiration catheter, a port 4260 is in fluid communication with the lumen 3176 of the distal supply tube 3168 (FIG. 34). Thus the port 4260 may be configured to be coupled to a source of pressurized fluid 4268 (e.g., normal saline). The connector 4261 is configured to be coupled to a connector 4263 at the distal end of a y-connector 4265. The connector 4263 may comprise a male luer. The y-connector 4265 includes a hemostasis valve 4267 (Touhy-Borst, spring-loaded seal, etc.) and a sideport 4269. The hemostasis valve 4267 is configured to seal around the guidewire 3102. The sideport 4269 of the y-connector 4265 is configured to be coupled to a vacuum source 4266. The sideport 4262 of y-connector 4244 may additionally be configured to be coupled to a vacuum source 4270, and/or may be used for injections of fluids, such as contrast media.

The aspiration catheter 3000 includes an open distal end 3158, which may include a skive 3162. The guidewire 3102 is shown in FIG. 38 having a distal end 3143 which includes a curved portion 3147 and a straight portion 3145, though other distal configurations are also contemplated, including curved only or straight only. The guidewire 3102 is shown extending through the aspiration lumen 3160 of the aspiration catheter 3000 and proximally through the connector 4254 and through the y-connector 4265. The guidewire 3102 may be secured at its proximal end 3188 to a rotatable chuck 4207, which is rotatably carried by the guidewire manipulation device 4231. The chuck 4207 may be manipulated to selectively grip and ungrip (engage and unengage, lock and unlock, etc.) the guidewire 3102 via a collet, or any equivalent means. The guidewire manipulation device 4231 is configured to be supported by the hand of a user, and includes the handle 4237 which has one or more controls 4243. The handle 4237 may extend in a generally perpendicular direction from the axis of the guidewire 3102 as it extends through the housing 4262, and may angle towards a distal end 4236 of the housing 4232 (as shown in FIG. 38) in a reverse gun handle grip. Alternatively, the handle 4237 may have a standard gun handle grip (see FIG. 37), and thus may angle towards a proximal end 4234 of the housing 4232. The controls 4243 are shown in FIG. 38 carried on a distally-facing surface 4239 of the handle 4237, and may be configured in this embodiment to be operated by one or more finger of the hand of the user, which may include non-thumb fingers. The controls 4243 may include an activation button 4214 which is configured to turn power on an off, for example, to power a motor (not shown) which is configured to rotate and/or longitudinally move the guidewire 3102. A control knob 4217 may be configured to increase or decrease a rotation speed (e.g., of the motor) or to select a plurality of different manipulation routines. The manipulation routines may be stored within memory that is carried within the guidewire manipulation device 4231, for example, on a circuit board. The circuit board may include a controller, as described in relation to the other embodiments herein. An exemplary manipulation routine may include rotating the guidewire 3102 in a first rotational direction eight rotations, and then rotating the guidewire 3102 in a second, opposite, rotational direction eight rotations. Another manipulation routine may include rotating continuously in a single direction. Another manipulation routine may include rotating continuously in one direction while repeatedly translating the guidewire 3102 distally and proximally (longitudinal cycling). Alternatively, the controls 4243 may be carried on a proximally-facing surface 4238 of the handle 4237, and may be configured to be operated primarily by the thumb of the hand of the user. The motor may be connected to the chuck 4207 directly, or by other drive elements, including gearing, which may be used to change speeds, torques, or rotational directions. The drive elements may include those described in relation to any of the embodiments disclosed herein. In use, the vacuum source 4266 may be coupled to the sideport 4269 of the y-connector 4265, and thrombus may thus be aspirated through the aspiration lumen 3160 of the aspiration catheter 3000. The vacuum source 4266 may comprise a syringe, a vacuum chamber, or a vacuum pump. Syringes with lockable plungers, for example syringes having volumes of between about 20 ml and about 30 ml, may be used as the vacuum source. While performing an aspiration procedure, the user may simultaneously or sequentially operate the guidewire manipulation device 4231 to rotate and/or longitudinally move the guidewire 3102, in order to aid the maceration of the thrombus and/or the movement of the thrombus or pieces of the thrombus through the aspiration lumen 3160.

Figure 37:
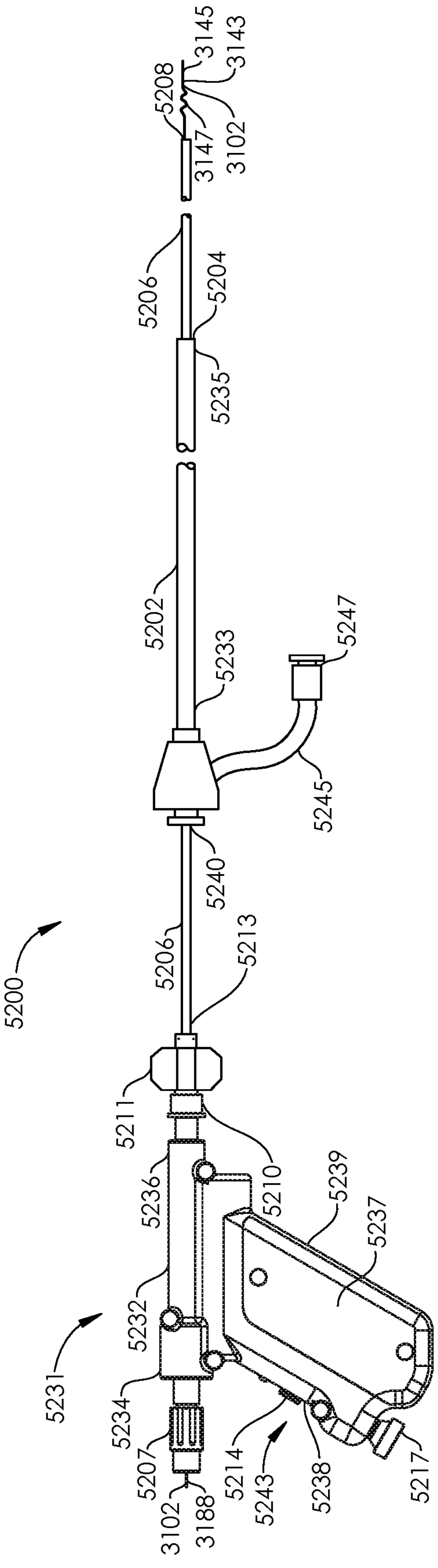
FIG. 37 illustrates a plan view of a system for treating a patient having thrombus, according to an embodiment of the present disclosure.

FIG. 37 illustrates a system for treating thrombus 5200. The system for treating thrombus 5200 includes a sheath 5202 having a lumen 5204 passing therethrough through which a microcatheter 5206 is placed. A guidewire 3102 may be inserted a lumen 5208 of the microcatheter 5206. The guidewire 3102 is configured to be manipulated (rotationally and/or longitudinally) by a guidewire manipulation device 5231 having a housing 5232 and a handle 5237. The guidewire manipulation device 5231 may include any of the embodiments described herein, or may include embodiments of guidewire manipulation devices such as those disclosed in co-pending U.S. patent application Ser. No. 15/235,920, filed on Aug. 12, 2016 and entitled "System and Method for Manipulating an Elongate Medical Device." The housing 5232 has a proximal end 5234 and a distal end 5236 and the handle 5237 extends in a substantially radial direction from the guidewire axis of the housing 5232. Controls 5243 are carried by a proximally-facing surface 5238, and include an activation button 5214 and a control knob 5217, which may be configured similar to the activation button 4214 and the control knob 4217 of the guidewire manipulation device 4231 of the embodiment of FIG. 38. The user's hand is configured to grip the standard gun handle grip of the handle 5237 by wrapping around the distally-facing surface 5239. The handle 5237 is depicted in FIG. 37 angling toward the proximal end 5234 of the housing 5232. The user may operate the controls 5243 using the user's thumb, or a combination of the user's thumb and one of the non-thumb fingers of the user's hand. A chuck 5207 is carried by the guidewire manipulation device 5231 adjacent the proximal end 5234 of the housing 5232 and is configured to rotate and/or longitudinally move the guidewire 3102 in a similar manner to the chuck 4207 of FIG. 38. However, the guidewire 3102 is configured to pass through the housing 5232 and a proximal end 3188 of the guidewire 3102 is configured to be secured to the chuck 5207. The guidewire manipulation device 4231 includes a locking element 5210 carried adjacent the distal end 5236 of the housing 5232 which is connectable to a connector 5211 which is coupled to a proximal end 5213 of the microcatheter 5206. The locking element 5210 and the connector 5211 comprise male and female luer locks, or may comprise other types of locking connections which secure the connector 5211 with respect to the guidewire manipulation device 5231. When the locking element 5210 and the connector 5211 are secured to each other, relative rotational and/or longitudinal motion between the guidewire manipulation device 5231 and the connector 5211 are inhibited. The sheath 5202 includes a proximal end 5233 and a distal end 5235, and may include a proximal internal seal 5241, and a sideport 5245 having a luer 5247. In use, the user may operate the guidewire manipulation device 5231 (for example, by holding the handle 5237 and pressing the activation button 5214) while also moving pushing or pulling the microcatheter 5206 within the lumen 5204 of the sheath 5202. Thrombus may be macerated by the distal end 3143 of the guidewire 3102. If desired, the thrombus may be aspirated through the lumen 5204 of the sheath 5202, by applying a vacuum (e.g., attaching a vacuum source, not shown) to the sideport 5245 of the sheath 5202. The sheath 5202 may also be moved proximally or distally so that the distal end 5235 of the sheath approaches the thrombus or portions of thrombus or blood to be aspirated. If desired, the locking element 5210 of the guidewire manipulation device 5231 may be detached from the connector 5211 of the microcatheter 5206, and a vacuum source (not shown) may be attached to the connector 5211 in order to aspirate thrombus or blood through the lumen 5208 of the microcatheter 5206.

Figure 36:
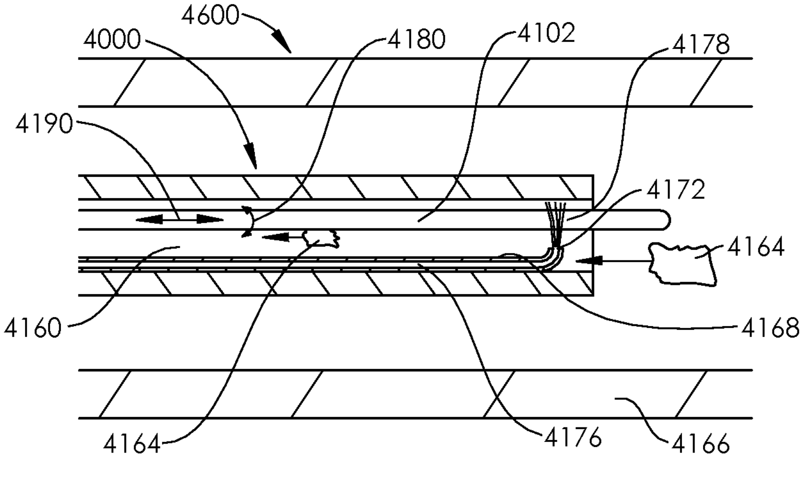
FIG. 36 illustrates an aspiration catheter within a blood vessel used in conjunction with a guidewire which is moved by a guidewire manipulation device, according to another embodiment of the present disclosure.

FIG. 36 illustrates an aspiration catheter 4000 within a blood vessel 4600 having a blood vessel wall 4166. The aspiration catheter 4000 has an aspiration lumen 4160 which is configured for aspirating thrombus 4164 and also for placement of a guidewire 4102 which is configured to track the aspiration catheter 4000 through the vasculature of a patient. A distal supply tube 4168 having a lumen 4176 is configured for injecting pressurized fluid, such as saline. The pressurized fluid is injected through the lumen 4176 and out an orifice 4172 into the aspiration lumen 4160. The orifice is located at the extreme distal end of the distal supply tube 4168. The output of the pressurized fluid through the orifice 4172 may comprise a jet 4178. Thrombus 4164 is aspirated into the aspiration lumen 4160. In some embodiments, the jet 4178 macerates the thrombus 4164 as it passes by the jet 4178. The guidewire 4102 may be attached to the guidewire manipulation device 100, 132, 140, 170, 190, 220, 2100, 650, 1100, 4231 and moved by the guidewire manipulation device 100, 132, 140, 170, 190, 220, 2100, 650, 1100, 4231 in one or more patterns including rotation motion 4180 and/or longitudinal motion 4190. Either or both of these motions may be imparted on the guidewire 4102 to conjunctively aid the maceration of the thrombus 4164, and/or to aid in the transport of the thrombus 4164 from distal to proximal through the aspiration lumen 4160. The rotational motion 4180 may include clockwise only, counter-clockwise only, or a combination of clockwise and counter-clockwise, for example back and forth rotational oscillation as described herein. The longitudinal motion 4190 may be movement imparted directly on the guidewire 4102 by the operation of the guidewire manipulation device 100, 132, 140, 170, 190, 220, 2100, 650, 1100, 4231, or may be manually applied by the user by moving the guidewire manipulation device 100, 132, 140, 170, 190, 220, 2100, 650, 1100, 4231 back and forth (distally and proximally). In some cases, the guidewire manipulation device 100, 132, 140, 170, 190, 220, 2100, 650, 1100, 4231 may be gradually pulled while the guidewire 4102 is rotated by the guidewire manipulation device 100, 132, 140, 170, 190, 220, 2100, 650, 1100, 4231. In some cases, the handle of the guidewire manipulation device can be cyclically moved distally and proximally while generally pulling the guidewire manipulation device 100, 132, 140, 170, 190, 220, 2100, 650, 1100, 4231 proximally. For example, one cm distally, two cm proximally, one cm distally, two cm proximally, etc. In some embodiments, the aspiration catheter 4000 may consist only of a single lumen for aspiration and guidewire placement, without any forced injection (i.e., no distal supply tube 4168). In some embodiments, the manipulation of the guidewire 4102 by the guidewire manipulation device 100, 132, 140, 170, 190, 220, 2100, 650, 1100, 4231 performs a similar function to a "separator device" as is used with the ACE™ or INDIGO® aspiration catheters produced by Penumbra, Inc. of Alameda, Calif., USA. The "separator device" is a guidewire type device with a ball or football-shaped portion at its tip that extends from an aspiration lumen and is pulled against the distal port of the aspiration lumen to help disrupt or macerate the thrombus/clot.

A variety of different elongate medical devices may be rotated, longitudinally moved, or otherwise manipulated by the embodiments of the guidewire manipulation device 100, 132, 140, 170, 190, 220, 2100, 650, 1100, 4231 described herein, including embodiments of the elongated medical instrument and the macerator which are disclosed in U.S. Patent Application Publication No. 2014/0142594 to Fojtik, published May 22, 2014, which is incorporated herein by reference in its entirety for all purposes.

In one embodiment a manipulation device includes a housing configured to be supported by the hand of a user, the housing having a distal end and a proximal end, a drive system disposed within the housing and configured to rotate a rotation member, an engagement member coupled to the rotation member and configured to be remotely coupled to an elongate medical device to transfer rotational movement of the rotation member to rotational movement of an elongate medical device, an activation member carried by the housing such that the activation member can be operated by at least a portion of the hand of the user when the housing is supported by the hand of the user, and wherein the drive system is configured to apply a combination of motive force components to the engagement member. In some embodiments, the combination of motive force components includes an alternating clockwise motion and counter-clockwise motion. In some embodiments, the combination of motive force components comprises a rotational motion and a cyclic longitudinal motion. In some embodiments, the activation member comprises a handle coupled to the housing and configured to be operable by the hand of the user. In some embodiments, the handle is configured to couple to the drive system mechanically. In some embodiments, the rotation member includes a tube having a window. In some embodiments, the manipulation device further includes a motor operatively coupled to the drive system, wherein the activation member is configured to initiate operation of the motor. In some embodiments, the manipulation device further includes gearing coupled to the motor. In some embodiments, the activation member includes a switch. In some embodiments, the elongate medical device consists of at least one of a guidewire, a basket, an expandable device, a catheter shaft, a macerator, or a cutting device. In some embodiments, the combination of motive force components comprises a helical motion. In some embodiments, the combination of motive force components comprises a jackhammer motion.

In another embodiment, a method for treating a patient having thrombus comprises providing a manipulation device comprising a housing configured to be supported by the hand of a user, the housing having a distal end and a proximal end, a drive system disposed within the housing and configured to rotate a rotation member, an engagement member coupled to the rotation member, and configured to be removably coupled to an elongate medical device, an activation member carried by the housing such that it can be operated by at least a portion of the hand of the user when the housing is supported by the hand of the user, and wherein the drive system is configured to apply motive force to the engagement member, securing an elongate member to the engagement member, the elongate member having a distal end configured for introduction into a patient's vasculature, introducing at least the distal end of the elongate member into a blood vessel adjacent a thrombus, operating the activation member to cause at least some rotation of the rotation member, which in turn causes at least some rotation of the distal end of the elongate member at or near the thrombus, and aspirating at least some thrombus with an aspiration catheter. In some embodiments, the motive force comprises a combination of motive force components including an alternating clockwise motion and counter-clockwise motion. In some embodiments, the combination of motive force components comprises a rotational motion and a cyclic longitudinal motion. In some embodiments, the activation member comprises a handle coupled to the housing and configured to be operable by the hand of the user. In some embodiments, the handle is configured to couple to the drive system mechanically. In some embodiments, the rotation member comprises a tube including a window. In some embodiments, the manipulation device further comprises a motor operatively coupled to the drive system, wherein the activation member is configured to initiate operation of the motor. In some embodiments, the manipulation device further comprises gearing coupled to the motor. In some embodiments, the activation member comprises a switch. In some embodiments, the elongate medical device consists of at least one of a guidewire, a basket, an expandable device, a catheter shaft, a macerator, and a cutting device. In some embodiments, the combination of motive force components comprises a helical motion. In some embodiments, the combination of motive force components comprises a jack-hammer motion. In some embodiments, the elongate member comprises a guidewire. In some embodiments, the distal end of the elongate member is substantially straight. In some embodiments, the distal end of the elongate member is curved. In some embodiments, at least a portion of the aspiration catheter extends alongside at least a portion of the elongate member within a delivery lumen of a delivery catheter. In some embodiments, the at least some rotation of the distal end of the elongate member facilitates movement of the thrombus through the delivery lumen of the delivery catheter. In some embodiments, the delivery catheter is a coronary guiding catheter. In some embodiments, the elongate member extends within a lumen of the aspiration catheter. In some embodiments, the elongate member extends within an aspiration lumen of the aspiration catheter. In some embodiments, the elongate member is rotatable within the lumen of the aspiration catheter. In some embodiments, the at least some rotation of the distal end of the elongate member facilitates movement of the thrombus through the lumen of the aspiration catheter. In some embodiments, the aspiration catheter comprises a supply lumen and an aspiration lumen, the supply lumen having a wall and a closed distal end, the aspiration lumen configured to couple to a vacuum source and having an interior wall surface and an open distal end, the wall of the supply lumen having an orifice in fluid communication with the interior of the aspiration lumen, the orifice located proximally of the open end of the aspiration lumen and adjacent the closed distal end of the supply lumen. In some embodiments, the method further comprises providing a tubing set having a first conduit configured to couple the supply lumen of the aspiration catheter to a fluid source, and a pump component associated with the first conduit and configured to detachably couple to a drive unit, such that the motion from the drive unit is transferred to the pump component such that resultant motion of the pump component causes fluid from the fluid source to be injected through the supply lumen of the aspiration catheter, and through the orifice into the aspiration lumen. In some embodiments, the pump comprises a piston. In some embodiments, the orifice is configured to create a spray pattern when pressurized fluid is pumped through the supply lumen such that the spray pattern impinges on the interior wall surface of the aspiration lumen. In some embodiments, the aspiration catheter comprises a tubular aspiration member having a proximal end, a distal end, and a lumen, and configured to at least partially extend out of the lumen of a delivery catheter having a lumen, and into the vasculature of a subject, an elongate support member coupled to the tubular aspiration member and extending between a proximal end of the aspiration catheter and the proximal end of the tubular aspiration member, and an annular seal comprising at least one annular sealing member coupled to the tubular aspiration member.

In another embodiment, a method for breaking up a thrombus or embolus comprises providing a manually-operated guidewire manipulation device comprising a housing having a proximal end, an elongate body, and a distal end, a rotation member disposed within the housing and configured to rotate with respect to the housing, a locking assembly operably coupled to a distal end of the rotation member, the locking assembly having a locked mode wherein the rotation member is engaged with the guidewire, and an unlocked mode wherein the rotation member is disengaged from the guidewire, a handle coupled to the housing and configured to be operable by one hand of a user, and a drive system operably coupled to the handle, the drive system configured to rotate the rotation member upon actuation of the handle by the one hand of the user in a first direction with respect to the housing, thereby causing the guidewire to rotate in a first rotational direction when the locking assembly is in the locked mode, wherein the handle is configured to be releasable by the user such that the handle when released moves in a second direction with respect to the housing, the second direction opposite from the first direction, wherein the handle is configured to cause rotation of the rotation member in a second rotational direction opposite the first rotational direction when the handle moves in the second direction, thereby causing the guidewire to rotate in the second rotational direction, securing a guidewire to the rotation member via the locking assembly, the guidewire having a distal end extending through the lumen of a catheter and into a patient's vasculature, operating the manually-operated guidewire manipulation device to cause at least some rotation of the rotation member, which in turn causes at least some rotation of the guidewire, and aspirating at least some thrombus or embolus through the lumen of the catheter. In some embodiments, the catheter is an aspiration catheter. In some embodiments, the lumen is an aspiration lumen. In some embodiments, the aspiration lumen is also a guidewire lumen. In some embodiments, the catheter is a guiding catheter.

In some embodiments described herein, instead of a chuck being rotated, luer lock connector may instead be rotated. For example, a rotatable male luer lock connector may be coupled to a medical device (such as an elongated medical device, which may include a catheter), in order to rotated the medical device.

In some embodiments, the medical device to be rotated, axially displaced or moved in any other pattern may comprise one or more of: a drill bit, a burr, for example, burr systems for specialized Craniotomy use. In some embodiments, the system may include a safety stop. In some embodiments, the medical device to be rotated, axially displaced or moved in any other pattern may comprise one or more of: a tapered tip device that is advanced by spinning (for example a skived catheter), cutting tools for bone work, gigli saw wires, hollow trephines for biopsy (flexible or rigid), dissecting elements that slide or find channels (and may in some cases be able to expand), retriever expanding stent-like structures to penetrate thrombus and subsequently expand once in place, balloon like or other expandable structures that deliver drugs by rubbing against a vessel wall either by axial motion, rotation or a combination. It can be appreciated that by connection to any of the embodiments described herein, medical devices of a variety of types may be manipulated into motion such as rotating (one or more rotational directions), and pecking (forward and back). Additionally, oscillating action may be used in a coaxial system to move two elements in relation to each other, to release particles, drugs, or other materials. In some embodiments, the medical device to be rotated, axially displaced or moved in any other pattern may comprise one or more of: an endoscopic trocar introducer, via wire, a Veress needle introducer, a female uterine cervix fallopian tube traversing device for i.e. sterility device implantation, a ureter traversing for i.e. kidney stone manipulation, a filing system for root canals, a FESS (functional endoscopic sinus surgery) or burr-like surgical device, a sinusoidal/nasal access, a plastic surgery device for tunneling under layers of skin dermis, fat, a neurosurgical nose access device, a deep brain access device, for example a University of Pennsylvania Deep Brain Stimulation (DBS) device. In some embodiments, the medical device to be rotated, axially displaced or moved in any other pattern may comprise one or more of: a hollow fenestrated wire drug delivery which delivers drugs while spinning, drugs such as G2B3 Inhibitors which may be delivered at or into thrombus. In some embodiments, the medical device to be rotated, axially displaced or moved in any other pattern may comprise one or more of: an aneurysmal wire/catheter navigation and liquid embolic dispensing device.

While the foregoing is directed to embodiments of the present disclosure, other and further embodiments may be devised without departing from the basic scope thereof.

What is claimed is:

1. A method for treating a patient having thrombus comprising:
- providing a manipulation device comprising:
  - a housing configured to be supported by a hand of a user, the housing having a distal end and a proximal end;
  - a drive system disposed within the housing, and configured to rotate a rotation member;
  - an engagement member coupled to the rotation member, and configured to be releasably coupled to an elongate member to transfer rotational movement of the rotation member to rotational movement of the elongate member;
  - an activation member carried by the housing such that it can be operated by at least a portion of the hand of the user when the housing is supported by the hand of the user; and
  - wherein the drive system is configured to apply motive force to the engagement member such that the elongate member may thereby be rotated in a clockwise direction and rotated in a counter-clockwise direction;
- securing an elongate medical device to the engagement member, the elongate medical device having a distal end configured for introduction into a patient's vasculature;
- introducing at least the distal end of the elongate medical device into a blood vessel of a subject, adjacent a thrombus;
- operating the activation member to cause the drive system to rotate the rotation member, in turn causing alternating clockwise rotation and counter-clockwise rotation of the distal end of the elongate medical device at or near the thrombus to disrupt at least some of the thrombus; and
- aspirating at least some of the disrupted thrombus from the subject with an aspiration catheter.

2. The method of claim 1, wherein the drive system is configured to apply motive force to the engagement member such that cyclic longitudinal motion is imparted to the elongate member.

3. The method of claim 2, further comprising operating the activation member to cause the drive system to move the elongate medical device back and forth longitudinally.

4. The method of claim 1, wherein the elongate medical device is an expandable device.

5. The method of claim 1, wherein the elongate medical device comprises a catheter shaft.

6. The method of claim 1, wherein the elongate medical device comprises a macerator.

7. The method of claim 1, further comprising placing the elongate medical device through a lumen of the aspiration catheter.

8. The method of claim 7, wherein the lumen of the aspiration catheter is an aspiration lumen through which the disrupted thrombus is aspirated.

9. The method of claim 8, wherein the rotation of the elongate medical device within the aspiration lumen of the aspiration catheter facilitates movement of the disrupted thrombus through the aspiration lumen.

10. The method of claim 8, wherein the elongate medical device comprises a first portion configured to help center or stabilize the elongate member within the aspiration lumen.

11. A method for treating a patient having thrombus comprising:
- providing a manipulation device comprising:
  - a housing configured to be supported by a hand of a user, the housing having a distal end and a proximal end;
  - an engagement member rotatable in relation to the housing, and configured to be releasably coupled to an elongate member to transfer rotational movement to the elongate member;
  - a drive system disposed within the housing, and configured to rotate the engagement member;
  - an activation member carried by the housing such that it can be operated by at least a portion of the hand of the user when the housing is supported by the hand of the user; and
  - wherein the drive system is configured to apply motive force to the engagement member such that the elongate member may thereby be rotated in a clockwise direction and rotated in a counter-clockwise direction;
- securing an elongate medical device to the engagement member, the elongate medical device having a distal end configured for introduction into a patient's vasculature;
- introducing at least the distal end of the elongate medical device into a blood vessel of a subject, adjacent a thrombus;
- operating the activation member to cause the drive system to rotate the engagement member in relation to the housing, in turn causing alternating clockwise rotation and counter-clockwise rotation of the distal end of the elongate medical device at or near the thrombus to disrupt at least some of the thrombus; and aspirating at least some of the disrupted thrombus from the subject with an aspiration catheter.

12. The method of claim 11, wherein the drive system is configured to apply motive force to the engagement member such that cyclic longitudinal motion is imparted to the elongate member.

13. The method of claim 12, further comprising operating the activation member to cause the drive system to move the elongate medical device back and forth longitudinally.

14. The method of claim 11, wherein the elongate medical device is an expandable device.

15. The method of claim 11, wherein the elongate medical device comprises a catheter shaft.

16. The method of claim 11, wherein the elongate medical device comprises a macerator.

17. The method of claim 11, further comprising placing the elongate medical device through a lumen of the aspiration catheter.

18. The method of claim 17, wherein the lumen of the aspiration catheter is an aspiration lumen through which the disrupted thrombus is aspirated.

19. The method of claim 18, wherein the rotation of the elongate medical device within the aspiration lumen of the aspiration catheter facilitates movement of the disrupted thrombus through the aspiration lumen.

20. The method of claim 18, wherein the elongate medical device comprises a first portion configured to help center or stabilize the elongate member within the aspiration lumen.

* * * * *